US008227476B2

(12) United States Patent
Ceci et al.

(10) Patent No.: US 8,227,476 B2
(45) Date of Patent: Jul. 24, 2012

(54) USE OF FLIBANSERIN IN THE TREATMENT OF OBESITY

(75) Inventors: Angelo Ceci, Mittelbiberach (DE); Marcus Schindler, Biberach (DE)

(73) Assignee: Sprout Pharmaceuticals, Inc., Raleigh, NC (US)

( * ) Notice: Subject to any disclaimer, the term of this patent is extended or adjusted under 35 U.S.C. 154(b) by 0 days.

(21) Appl. No.: 11/997,567

(22) PCT Filed: Jul. 31, 2006

(86) PCT No.: PCT/EP2006/064825
§ 371 (c)(1),
(2), (4) Date: Mar. 21, 2008

(87) PCT Pub. No.: WO2007/014929
PCT Pub. Date: Feb. 8, 2007

(65) Prior Publication Data
US 2008/0242678 A1    Oct. 2, 2008

(30) Foreign Application Priority Data

Aug. 3, 2005   (EP) ..................................... 05016867

(51) Int. Cl.
*A61K 31/517* (2006.01)
*A61K 31/415* (2006.01)
(52) U.S. Cl. .................. 514/266.22; 514/394; 514/395; 514/909
(58) Field of Classification Search ............. 514/266.22, 514/394, 395, 909
See application file for complete search history.

(56) References Cited

U.S. PATENT DOCUMENTS

| | | |
|---|---|---|
| 3,096,248 A | 7/1963 | Rudzki |
| 3,406,178 A | 10/1968 | Crocker et al. |
| 3,472,854 A | 10/1969 | Archer |
| 4,200,641 A | 4/1980 | Vandenberk et al. |
| 4,367,217 A | 1/1983 | Gruber et al. |
| 4,737,500 A | 4/1988 | Sorg |
| 4,792,452 A | 12/1988 | Howard et al. |
| 4,797,399 A | 1/1989 | Ueda et al. |
| 4,859,692 A | 8/1989 | Bernstein et al. |
| 4,886,803 A | 12/1989 | Sueda et al. |
| 4,940,793 A | 7/1990 | Botrè et al. |
| 4,954,503 A | 9/1990 | Strupczewski et al. |
| 4,968,508 A | 11/1990 | Oren et al. |
| 5,002,948 A | 3/1991 | Perregaard et al. |
| 5,036,088 A | 7/1991 | Kitaura et al. |
| 5,225,417 A | 7/1993 | Dappen et al. |
| 5,405,642 A | 4/1995 | Gilis et al. |
| 5,407,686 A | 4/1995 | Patel et al. |
| 5,434,156 A | 7/1995 | Björk et al. |
| 5,492,907 A | 2/1996 | Pickar et al. |
| 5,552,412 A | 9/1996 | Cameron et al. |
| 5,576,318 A | 11/1996 | Bietti et al. |
| 5,591,743 A | 1/1997 | Patoiseau et al. |
| 5,854,290 A | 12/1998 | Arnsten et al. |
| 5,883,094 A | 3/1999 | Fliri et al. |
| 5,916,916 A | 6/1999 | Hauser et al. |
| 5,929,054 A | 7/1999 | Baker et al. |
| 5,977,106 A | 11/1999 | Patoiseau et al. |
| 6,068,846 A | 5/2000 | Cho et al. |
| 6,083,947 A | 7/2000 | Granger et al. |
| 6,165,513 A | 12/2000 | Dansereau et al. |
| 6,187,340 B1 | 2/2001 | Fukuta et al. |
| 6,281,218 B1 | 8/2001 | Cereda et al. |
| 6,284,757 B1 | 9/2001 | Sanner |
| 6,346,548 B1 | 2/2002 | Miller et al. |
| 6,426,087 B1 | 7/2002 | Saslawski et al. |
| 6,482,841 B1 | 11/2002 | Letelier et al. |
| 6,521,623 B1 | 2/2003 | Cereda et al. |
| 6,586,435 B2 | 7/2003 | Cereda et al. |
| 6,627,646 B2 | 9/2003 | Bakale et al. |
| 6,680,071 B1 | 1/2004 | Johnson et al. |
| 7,151,103 B2 | 12/2006 | Borsini et al. |
| 7,183,410 B2 | 2/2007 | Bombarda et al. |
| 7,420,057 B2 | 9/2008 | Bombarda et al. |
| 2002/0001397 A1 | 1/2002 | Ishikawa et al. |
| 2002/0010216 A1 | 1/2002 | Rogosky et al. |
| 2002/0103208 A1 | 8/2002 | Cereda et al. |
| 2002/0151543 A1 | 10/2002 | Barberish et al. |
| 2003/0027823 A1 | 2/2003 | Cereda et al. |
| 2003/0060475 A1 | 3/2003 | Borsini |
| 2003/0083228 A1 | 5/2003 | Carpino et al. |
| 2003/0104980 A1 | 6/2003 | Borsini et al. |
| 2003/0119850 A1 | 6/2003 | Bombarda et al. |
| 2004/0023948 A1 | 2/2004 | Green et al. |
| 2004/0048877 A1 | 3/2004 | Friedl et al. |

(Continued)

FOREIGN PATENT DOCUMENTS

BE    904945    12/1986

(Continued)

OTHER PUBLICATIONS

Aizenberg et al, "Cyproheptadine Treatment of Sexual Dysfunction Induced by Serotonin Reuptake Inhibitors," Clinical Neuropharmacology, vol. 18, No. 4, pp. 320-324, 1995 Lippincott-Raven Publishers, Philadelphia.
Archer, T.; "5-HT, Pain and Anxiety" Behavioural Pharmacology of 5-HT, pp. 299-300 (1989).
Chemical Abstract 88-98788c (Apr. 10, 1978),Awouters et al, "Oxatomide, a new orally active drug which inhibits both the release and the effects of allergic mediators."
Backhauss et al., "A Mouse Model of Focal Cerebral Ischemia for Screening Neuroprotective Drug Effects," Journal of Pharmacological Methods 27, 1992, pp. 27-32.
Basson, R. et al; "Report of the international consensus development conference on female sexual dysfunction: definitions and classifications;" The Journal of Urology; vol. 163 pp. 888-893, Mar. 2000.

(Continued)

*Primary Examiner* — Kevin E Weddington
(74) *Attorney, Agent, or Firm* — Summa, Additon & Ashe, P.A.

(57) ABSTRACT

The invention relates to a method for the treatment of obesity and related diseases comprising the administration of a therapeutically effective amount of Flibanserin.

5 Claims, No Drawings

U.S. PATENT DOCUMENTS

| | | | |
|---|---|---|---|
| 2004/0116532 A1 | 6/2004 | Heacock et al. |
| 2004/0132697 A1 | 7/2004 | Thurlow et al. |
| 2004/0147581 A1 | 7/2004 | Taylor et al. |
| 2004/0180904 A1 | 9/2004 | Beck |
| 2004/0193452 A1 | 9/2004 | Berman |
| 2004/0235861 A1 | 11/2004 | Borsini |
| 2004/0258749 A1 | 12/2004 | Guldner et al. |
| 2005/0004105 A1 | 1/2005 | Leahy et al. |
| 2005/0037983 A1 | 2/2005 | Dinan et al. |
| 2005/0065158 A1 | 3/2005 | Naylor et al. |
| 2005/0095293 A1 | 5/2005 | Brauns et al. |
| 2005/0159430 A1 | 7/2005 | Bombarda et al. |
| 2005/0239798 A1 | 10/2005 | Pyke |
| 2005/0245539 A1 | 11/2005 | Mendla et al. |
| 2006/0014757 A1 | 1/2006 | Pyke |
| 2006/0025420 A1 | 2/2006 | Brauns et al. |
| 2006/0052391 A1 | 3/2006 | Dolsten |
| 2006/0160822 A1 | 7/2006 | Borsini |
| 2006/0199805 A1 | 9/2006 | Pyke et al. |
| 2006/0204486 A1 | 9/2006 | Pyke et al. |
| 2006/0211685 A1 | 9/2006 | Pyke et al. |
| 2006/0252773 A1 | 11/2006 | Ceci et al. |
| 2006/0258640 A1 | 11/2006 | Ceci et al. |
| 2006/0264511 A1 | 11/2006 | Pyke |
| 2006/0264512 A1 | 11/2006 | Pyke |
| 2007/0032654 A1 | 2/2007 | Bombarda et al. |
| 2007/0032655 A1 | 2/2007 | Bombarda et al. |
| 2007/0072872 A1 | 3/2007 | Borsini et al. |
| 2007/0105869 A1 | 5/2007 | Pollentier et al. |
| 2007/0123540 A1 | 5/2007 | Ceci |
| 2007/0196473 A1 | 8/2007 | Friedl et al. |
| 2007/0265276 A1 | 11/2007 | Pollentier et al. |
| 2008/0038346 A1 | 2/2008 | Eisenreich et al. |
| 2008/0038347 A1 | 2/2008 | Eisenreich et al. |
| 2008/0069873 A1* | 3/2008 | Pearnchob et al. ............ 424/459 |
| 2008/0103155 A1 | 5/2008 | Mendla et al. |
| 2008/0119482 A1 | 5/2008 | Dolsten |
| 2008/0242678 A1 | 10/2008 | Ceci et al. |
| 2008/0242679 A1 | 10/2008 | Ceci |
| 2009/0023712 A1 | 1/2009 | Ferger et al. |
| 2009/0054458 A1 | 2/2009 | Bombarda et al. |
| 2009/0176698 A1 | 7/2009 | Baiker et al. |
| 2009/0239881 A1 | 9/2009 | Becker |
| 2009/0247546 A1 | 10/2009 | Ceci et al. |
| 2009/0312242 A1 | 12/2009 | Castro et al. |
| 2009/0318469 A1 | 12/2009 | Pyke et al. |

FOREIGN PATENT DOCUMENTS

| | | |
|---|---|---|
| CA | 2455628 A1 | 2/2003 |
| CL | 1033-1999 | 5/1999 |
| CL | 2394-1999 | 10/1999 |
| CL | 1491-2001 | 6/2001 |
| CL | 2833-2001 | 11/2001 |
| CL | 418-2002 | 3/2002 |
| CL | 1706-2002 | 7/2002 |
| CL | 1878-2002 | 8/2002 |
| CL | 2389-2002 | 10/2002 |
| CL | 1751-2004 | 7/2004 |
| CL | 911-2005 | 4/2005 |
| CN | 1571670 A | 1/2005 |
| CN | 1655789 A | 8/2005 |
| DE | 3620643 A1 | 1/1987 |
| DE | 10209982.0 | 3/2002 |
| DE | 10138273 A1 | 2/2003 |
| EP | 0200322 A1 | 11/1986 |
| EP | 0376607 A1 | 7/1990 |
| EP | 0497985 A1 | 8/1992 |
| EP | 0526434 B1 | 2/1993 |
| EP | 0705832 A1 | 4/1996 |
| EP | 0816356 A1 | 1/1998 |
| EP | 0982030 A2 | 3/2000 |
| EP | 1256343 A1 | 11/2002 |
| EP | 1285658 | 2/2003 |
| EP | 1285658 A2 | 2/2003 |
| EP | 1014985 | 5/2003 |
| EP | 1518858 A1 | 3/2005 |
| EP | 1674102 | 6/2006 |
| GB | 2023594 A | 1/1980 |
| IE | 1992/1340 | 10/1992 |
| IL | 159151 | 2/2003 |
| IL | 160389 | 2/2004 |
| JP | 8-143476 | 6/1996 |
| RU | 93014306 A | 3/1995 |
| WO | WO 9202215 A1 | 2/1992 |
| WO | 92/03167 A1 | 3/1992 |
| WO | 92/19606 A1 | 11/1992 |
| WO | 93/03016 A1 | 2/1993 |
| WO | 95/01965 A1 | 1/1995 |
| WO | WO 9519978 | 7/1995 |
| WO | 95/34555 A1 | 12/1995 |
| WO | 96/05834 A1 | 2/1996 |
| WO | 96/16949 A1 | 6/1996 |
| WO | WO 9819668 A1 | 5/1998 |
| WO | 98/33784 A1 | 8/1998 |
| WO | 98/42344 A1 | 10/1998 |
| WO | 99/19302 A1 | 4/1999 |
| WO | WO 9959593 A1 | 5/1999 |
| WO | WO 99/59584 A1 | 11/1999 |
| WO | 00/28993 A1 | 5/2000 |
| WO | WO 00/24383 A1 | 5/2000 |
| WO | WO 0063193 | 10/2000 |
| WO | 00/64441 A2 | 11/2000 |
| WO | WO 0067735 A2 | 11/2000 |
| WO | WO 0100224 A1 | 1/2001 |
| WO | 01/12170 A2 | 2/2001 |
| WO | 01/21593 A1 | 3/2001 |
| WO | WO 02/00654 A1 | 1/2002 |
| WO | 02/24662 A1 | 3/2002 |
| WO | WO 02/41894 A2 | 5/2002 |
| WO | WO 02/072586 A1 | 9/2002 |
| WO | 02/079143 A1 | 10/2002 |
| WO | WO 03007949 A1 | 1/2003 |
| WO | 03/011396 A1 | 2/2003 |
| WO | 03/013539 A1 | 2/2003 |
| WO | 03/014079 A1 | 2/2003 |
| WO | 03/035072 A1 | 5/2003 |
| WO | WO 03074032 A1 | 9/2003 |
| WO | 03/097058 A1 | 11/2003 |
| WO | 2004/041259 A1 | 5/2004 |
| WO | 2004/045509 A2 | 6/2004 |
| WO | 2004/069339 A1 | 8/2004 |
| WO | 2005/007166 A1 | 1/2005 |
| WO | WO 2005/007166 A1 | 1/2005 |
| WO | 2005/044238 A1 | 5/2005 |
| WO | 2005/087207 A1 | 9/2005 |
| WO | 2005/102343 A1 | 11/2005 |
| WO | 2005102342 A1 | 11/2005 |
| WO | 2006/010574 A1 | 2/2006 |
| WO | 2006019715 A1 | 2/2006 |
| WO | WO 2006024471 A1 | 3/2006 |
| WO | 2006/096435 A1 | 9/2006 |
| WO | WO 2006096434 A2 | 9/2006 |
| WO | 2006/125041 A1 | 11/2006 |
| WO | 2007/014929 A1 | 2/2007 |
| WO | WO 2007023325 A2 | 3/2007 |
| WO | 2007/048803 A1 | 5/2007 |
| WO | WO 2007090091 A2 | 8/2007 |
| WO | WO 2008006839 A | 1/2008 |
| WO | WO 2008022932 A2 | 2/2008 |

OTHER PUBLICATIONS

Baxter, G., "5-HT$_2$ Receptor Subtypes: a family re-united?", Trends in Pharmacological Sciences, Elsevier, Haywarth, GB, vol. 16, No. 3, Mar. 1995, pp. 105-110.

Beers, M.H. et al; The Merck Manual of Diagnosis and Therapy; 17th Ed., 1999, pp. 1595-1598.

Bernstein, J. et al; "Concomitant Polymorphs"; Angewandte Chemie, Int. Ed., 1999, pp. 3441-3461.

Bevan et al; "5-HT and sexual behaviour" Behavioural Pharmacology of 5-HT, pp. 33-34, 87-88 (1989).

Borsini, F. et al; Behavioral Effects of Flibanserin (BIMT 17), Sep. 1999, Pharmacology, Biochemistry and Behavior, vol. 64, Issue 1, abstract.

Borsini, F. et al; Behavioral Effects of Flibanserin (BIMT 17), Sep. 1999, Pharmacology Biochemistry and Behavior, vol. 64, Issue 1, pp. 137-146.

Borsini, F. et al; "Flibanserin," Drugs of the future, (1998) vol. 23 (1) pp. 9-16.

Borsini, F. et al; "BIMT 17, a 5-$HT_{2A}$ receptor antagonist and 5-$HT_{1A}$ receptor full agonist in rat cerebral cortex"; Naunyn-Schmiedeberg's Archives of Pharm., 1995, 352 pp. 276-282.

Borsini, F. et al; "Lack of interaction between flibanserin and antidepressants in inducing serotonergic syndrome in rats" International Journal of Neuropsychopharmacology (2001) pp. 9-15, vol. 4, No. 1, University Press, Cambridge, GB.

Borsini, F. et al, "Mechanism of action of flibanserin in the learned helplessness paradigm in rats," European Journal of Pharmacology 433:81-89 (2001).

Borsini, F. et al; "Pharmacology of Flibanserin" CNS Drug Reviews 2002; vol. 8, No. 2, pp. 117-142.

Borsini, F. et al., "BIMT 17: a putative antidepressant with a fast onset of action?" Psychopharmacology (1997) 134:378-386.

Brambilla et al., "Effect of Flibanserin (BIMT 17), fluoxetine 8-OH-DPAT and busprione on serotonin synthesis in rat brain," Europ. Neuropsychopharmacology, Vo. 10, No. 1, 1999, pp. 63-67.

Carey, John, "Viagra for Women?" Business Week.com (Dec. 28, 2006).

R. Cesana et al; "The effect of MIMT 17, a new potential antidepressant, in the forced swimming test in mice" Behavioral Pharmacology (1995) pp. 688-694, vol. 6. Rapid Science Publishers, GB.

Chalmers et al; "Corticotrophin-releasing factor receptors: from molecular biology to drug design" TiPS vol. 17 pp. 166-172, Apr. 1996.

Chemical Abstract: Database, Collino, F. et al; accession No. 98:16650: "Mannich bases of bensimidazoles, benzotriazoles and other analogous compounds, with pharmacological activity."—XP 002197885.

Cloninger, C.R.; "A systematic method for clinical description and classification of personality variants" Arch. Gen. Psychiatry, vol. 44 pp. 573-588 (Jun. 1987).

Cools, A.R.; "Depression and psychosis" Behavioural Pharmacology of 5-HT, pp. 153-155 (1989).

Crook, T. and Larkin, M.; "Effects of ondansertron in age-associated memory impairment" The role of ondansetron, a novel 5-HT3 antagonist, in the treatment of psychiatric disorders, 5th World Congress of Biochemical Psychiatry, pp. 21-23 (1991).

Cyr, Monica et al; "Nefazodone: Its place among antidepressants," Annals of Pharmacotherapy, vol. 30 No. 9 pp. 1006-1012; 1996.

Chemical Abstracts Service, Columbus 1978, Damir et al., "Hemodynamic effects of pharmacological block during acute overload of the heart" Database accession # 1978:591197 XP-002436715.

Chemical Abstract 118-124537e Damour et al, "Preparation and formulation of 1[(4-phenylpiperazino)alkyl]benzimidazolin-2-ones and analogs as serotonin $S_2$ antagonists" ( Mar. 29, 1993).

Darlington, C.; "Flibanserin Boehringer Ingelheim Corp."; Current Opinion in CPNS investigational drugs vol. 1, No. 4, 1999, pp. 510-513; Pharma Press Ltd, London, GB.

De Vry, J.;"5-$HT_{1A}$ receptors in psychopathology and the mechanism of action of clinically effective therapeutic agents" Drug News and Perspectives 1996, vol. 9 No. 5 pp. 270-280.

Deangelis, L.; "5-$HT_{2A}$ antagonists in psychiatric disorders;" Current Opinion in Investigational Drugs 2002; vol. 3 No. 1 pp. 106-112; ISSN: 1472-4472.

Dimmock, P. et al; "Efficacy of selective serotonin-reuptake inhibitors in premenstrual syndrome: A systematic review" The Lancet, vol. 356, No. 9236 pp. 1131-1136, Sep. 30, 2000.

Fourcroy, Jean L. ; "Female sexual dysfunction: potential for pharmaotherapy" Drugs 2003, vol. 63 No. 14 pp. 1445-1457.

Frampton, et al; "Pentoxifylline (Oxpentifylline) A Review of its Therapeutic Efficacy in the Management of Peripheral Vascular and Cerebrovascular Disorders;" (Drug Evaluation) Drugs and Aging 7 (6) pp. 480-503, 1995.

Fujikura et al; "Effects of naftidrofuryl oxalate, a 5-HT2 antagonist, on neuronal damage and local cerebral blood flow following transient cerebral ischemia in gerbils;" Brain Research 636 (1994) pp. 103-106.

Geyer, M.; "5-$HT_2$ antagonists increase tactile startle habituation in an animal model of habituation deficit in schizophrenia" Behavioural Pharmacology of 5-HT, pp. 243-246 (1989).

Giron, D; "Thermal analysis and calorimetric methods in the characterisation of polymorphs and solvates"; Thermochimica ACTA, Elsevier Science; 248; 1995; pp. 1-59.

Goa, et al; "Buspirone. A preliminary review of its pharmacological properties and therapeutic efficacy as an anxiolytic;" Drugs 1986 vol. 32 pp. 114-129.

Gonzales, "Natural Compound May Offer New Treatment for Chronic Pain" NIDA Notes, vol. 16, No. 3—Aug. 2001, www.nida.nih.gov/NIDA_Notes/NNVo116N3/Natural.htm.

Gould;"Salt selection for basic drugs;" International Journal of Pharmaceutics; vol. 33, Issue 1-3, pp. 201-217, Nov. 1986.

Greene, T.; "Protective groups in organic synthesis:", Harvard University pp. 10-17 (1981), Wiley-Interscience Publication).

Hansenne, M. et al; "Harm avoidance dimension of the tridimensional personality questionnaire and serotonin-1A activity in depressed patients;" Biol. Psychiatry 1997, vol. 42 pp. 959-961.

Invernizzi et al,"Flibanserin, a potential antidepressant drug, lowers 5-HT and raises dopamine and noradrenaline in the rat prefrontal cortex dialysate: role of 5-$HT_{1A}$ receptors"; British Journal of Pharmacology, vol. 139 pp. 1281-1288, Jun. 2003.

Kleven, M., "Modification of behavioral effects of 8-hydroxy-2-(di-n-propylamino) tetralin following chronic ethanol consumption in the rat: evidence for the involvement of 5-$HT_{1A}$ receptors in ethanol dependence.", European Journal of Pharmacology, 1995, vol. 281, No. 3, pp. 219-228.

Caplus abstract 1999:285050, KOBA, "Involvement of peripheral 5-$HT_{2A}$ receptor activation in pain behavior evoked by formalin paw injection in the rat," Kyushu Shika Gakkai Zaahi 53(1):253-60 (1999).

Lammers, GJ. et al; "Ritanserin, a 5-$HT_2$ receptor blocker, as add on treatment in narcolepsy;" Sleep 1991, vol. 14, No. 2 pp. 130-132.

Leonard, B.E.; "Sub-types of serotonin receptors: biochemical changes and pharmacological consequences" International Clinical Psychopharmacology 7, pp. 13-21 (1992).

Lyrer, "Neue Ansatze in der Akutbehandlung des zerebrovaskularen Insultes(New Approaches in the Acute Treatment of Cerebrovascular Insult)" Schweiz. Med. Wochenschr. vol. 124 No. 45 pp. 2005-2012 (1994).

Marazziti, Donatella et al; "Region-dependent effects of flibanserin and buspirone on adenylyl cyclase activity in the human brain" Int'l Journal of Neuropsychopharmacology, Jun. 2002, p. 131-140, vol. 5, No. 2.

Martindale: "Anxiolytic Sedatives Hypnotics and Antipsychotics" The complete drug reference, 1999, p. 635, Pharmaceutial Press, London 32.

McCall, RB. et al; "Role of serotonin 1A and serotonin 2 receptors in the central regulation of the cardiovascular system;" Pharmacological Reviews 1994, vol. 46 No. 3 pp. 231-243.

Merriam Webster New Collegiate Dictionary, definition of Diagnosis, 1981, p. 311.

Meston and Gorzalka, "Psychoactive Drugs and Human Sexual Behavior: The Role of Serotonergic Activity," Journal of Psychoactive Drugs, vol. 24(1), Jan.-Mar. 1992 pp. 1-40.

"The Merck Manual of diagnosis and therapy", Merck Research Laboratories, USA 1999, p. 1410, col. 1-p. 1413, col. 2, paragraph 1; p. 1412, tables 173-2 XP-002439435.

Miranda, et al., Dexketoprofen-Induced antinociception in animal models of acute pain: Synergy with morphine and paracetamol; Neuropharmacology 52 (2007) 291-296.

Moynihan, R., "The making of disease: female sexual dysfunction" British Medical Journal, 2003. vol. 326, pp. 45-47.

Nadeson, et al., "Antinociceptive role of 5-$HT_{1A}$ receptors in rat spinal cord" Laboratory Investigations, British Journal of Anaesthesia 88(5):679-84 (2002).

Okamoto et al., "5-HT2A receptor subtype in the peripheral branch of sensory fibers is involved in the potentiation of inflammatory pain in rats," Pain 99 (2002) 133-143.
Petkov, V.D. et al; "Participation of different 5-HT receptors in the memory process in rats and its modulation by the serotonin depletory p-chlorophenylalanine;" Acta Neurobiol. Exp. 1995 vol. 55 pp. 243-252.
Philips & Slaughter; "Depression and Sexual Desire," American Family Physician, vol. 62/No. 4, Aug. 15, 2000.
Podhorna, J. et al; "Flibanserin has anxiolytic effects without locomotor side effects in the infant rat ultrasonic vocalization model of anxiety;" British Journal of Pharacology (2000) vol. 130 No. 4 pp. 739-746.
Prehn et al; "Neuroprotective properties of 5-HT1A receptor agonists in rodent models of focal and global cerebral ischemia;" European Journal of Pharmacology, 203 (1991) 213-222.
Prehn et al., "Effects of serotonergic drugs in experimental brain ischemia: evidence for a protective role of serotonin in cerebral ischemia;" Brain Research 630 (1993) pp. 10-20.
Riekkinen et al; "The effects of increased serotonergic and decreased cholinergic activities on spatial navigation performance in rats" Pharmacology Biochemistry & Behavior, vol. 39 pp. 25-29 (1991).
Rueter, L.E. et al; "Electrophysiological examination of the effects of sustained flibanserin administration on serotonin receptors in rat brain;" British J. of Pharm, 1999, vol. 126, No. 3, pp. 627-638.
Risch, S. Craig et al; "Neurochemical alterations of serotonergic neuronal systems in depression;" J. Clin. Psychiatry 1992, vol. 53 No. 10 Suppl. 3-7.
Robinson, D.S. "Serotonin receptor subtypes and affective disorders;" Clinical Neuropharmacology 1993, vol. 16 No. Suppl. 3 pp. S1-S5.
Rosland et al., "The formalin test in mice: effect of formalin concentration," Pain 42 (1990) 235-242.
Shibata et al., "Ischemia-induced impairment of 2-deoxyglucose uptake and CA1 field potentials in rat hippocampal slices: protection by 5-HT1A receptor agonists and 5-HT2 receptor antagonists;" European Journal of Pharmacology, 229 (1992) pp. 21-29.
Shipton, B. et al., "Valvular heart disease: review and update," American Family Physician Jun. 1, 2001, vol. 63 # 11, pp. 2201-2208.
Sietsema, D. et al, "From Taboo to Treatment?" Good Clinical Practice Journal, Jan. 2005, vol. 12, # 1, pp. 23-27.
Spine-health.com, Types of Back Pain: Acute Pain, Chronic Pain and Neuropathic Pain, www.spine-health.com/topics/cd/chronic_pain/chronicpain02.html, Oct. 2, 2007.
Steiner, M., Recognition of Premenstrual Dysphoric Disorder and Its Treatment; The Lancet, vol. 356, No. 9236, Sep. 30, 2000, pp. 1126-1127.
Vandenberk et al; Piperazine and piperidine derivatives, Chemical Abstract 88-50920n (Jan. 30, 1978).
Walsh K. et al., "Sexual dysfunction in the older women and overview of the current understanding and management" Drugs and Aging, 2004, vol. 21, # 10 pp. 655-675.
Zajecka, John et al; "Sexual function and satisfaction in the treatment of chronic major depression with nefazodone, psychotherapy, and their combination;" Journal Clin. Psychiatry, vol. 63 No. 8 pp. 709-716, Aug. 2002.
U.S. Appl. No. 11/956,949, filed Dec. 14, 2007, D. Lewis-D'Agostino et.
U.S. Appl. No. 11/960,957, filed Dec. 20, 2007, Klaus Mendla et al.
U.S Appl. No. 11/940,655, filed Nov. 15, 2007; Dolsten, Mikael.
U.S. Appl. No. 12/091,848, filed Apr. 28, 2008, Ceci et al.
Cremers et al.; Non Erectile Dysfunction Application of Sildenafil; Herz; 2003; vol. 28; No. 4; pp. 325-333.
International Search Report (Form PCT/ISA/210) for corresponding PCT/EP2006/064825.
Anderson et al., Guidelines for choice of selective serotonin reuptake inhibitor in depressive illness, Adv. Psychia. Treatment, 2001, 7:170-180.
Freeman et al., Differential Response to Antidepressants in Women With Premenstrual Syndrome/Premenstrual Dysphoric Disorder, Arch Gen Phych, 1999, 56:932-939.
Yekimov, Sex toys and devices in sexual dysfunction therapy, www.mosmedclinic.ru/conf_library/2002/2/130/, 2002, 6 pgs.

Richelson, Pharmacology of Antidepressants, Mayo Clin Proc., 2001, 76:511-527.
Werneke et al., Antidepressants and sexual dysfuntion, Acta Psychia. Scand, 2005, 114:384-397.
Response to Final Office Action dated Aug. 17, 2010; U.S. Appl. No. 11/097,939, filed Apr. 4, 2005, 22 pgs.
RCE dated Aug. 17, 2010; U.S. Appl. No. 11/097,939, filed Apr. 4, 2005, 3 pgs.
RCE dated Sep. 27, 2010, U.S. Appl. No. 11/837,959, filed Aug. 13, 2007, 2 pg.
Response to Final Office Action dated Sep. 27, 2010, U.S. Appl. No. 11/837,959, filed Aug. 13, 2007, 20 pgs.
Response to Final Office Action dated Sep. 27, 2010 U.S. Appl. No. 11/278,551, filed Apr. 4, 2006, 8 pgs.
Interview Summary dated Jul. 19, 2010; U.S. Appl. No. 11/740,959, filed Apr. 27, 2007, 3pgs.
Final Office Action dated Aug. 20, 2010 U.S. Appl. No. 11/745,515, filed May 8 2007, 7 pgs.
Final Office Action dated Aug. 30, 2010 U.S Appl. No. 11/554,855, filed Oct. 31, 2006, 10 pgs.
Notice of Missing Requirements dated Aug. 24, 2010 U.S. Appl. No. 12/675,231, filed Feb. 25, 2010, 2 pgs.
Interview Summary dated Aug. 25, 2010 U.S. Appl. No. 11/278,551, filed Apr. 4, 2006, 3 pgs.
Final Office Action dated Sep. 13, 2010, U.S. Appl. No. 11/837,962, filed Aug. 13, 2007, 20 pgs.
Office Action dated Sep. 14, 2010; U.S. Appl. No. 11/097,939, filed Apr. 4, 2005, 18 pgs.
Interview Summary dated Sep. 15, 2010, U.S. Appl. No. 11/837,959, filed Aug. 13, 2007, 4 pg.
Notice of Allowance dated Sep. 20, 2010 U.S. Appl. No. 12/091,848, filed Apr. 28, 2008, 7 pgs.
Final Office Action dated Oct. 6, 2010; U.S. Appl. No. 11/837,957, filed Aug. 13, 2007, 10 pgs.
Response to Final Office Action dated Oct. 12, 2010; U.S. Appl. No. 11/960,957, filed Dec. 20, 2007, 16 pgs.
Briefing Document; Flibanserin (BIMT 17 BS); Boehringer Ingelheim; May 14, 2010; 248 pgs.
FDA (U.S. Food and Drug Administration); Reproductive Health Drugs Advisory Committee Meeting; Draft Agenda; Jun. 18, 2010; 1 pg.
FDA (U.S. Food and Drug Administration); Reproductive Health Drugs Advisory Committee Meeting; Draft Questions to the Committee; Jun. 18, 2010; 1 pg.
FDA (U.S. Food and Drug Administration); Reproductive Health Drugs Advisory Committee Meeting; Draft Meeting Roster; Jun. 18, 2010; 2 pgs.
Advisory Committee for Reproductive Health Drugs—2010 Members; Jun. 2010; 2 pgs.
FDA (U.S. Food and Drug Administration); Reproductive Health Drugs Advisory Committee Meeting; Agenda; Jun. 18, 2010; 2 pgs.
FDA (U.S. Food and Drug Administration); Reproductive Health Drugs Advisory Committee Meeting; Questions to the Committee; Jun. 18, 2010; 1 pgs.
FDA (U.S. Food and Drug Administration); Reproductive Health Drugs Advisory Committee Meeting; Meeting Roster; Jun. 18, 2010; 2 pgs.
(Slides) Division of Reproductive and Urologic Drug Products Advisory Committee Meeting; Flibanserin (NDA-22526); Boehringer Ingelheim; Jun. 18, 2010; 110 pgs.
Press Release May 19, 2010; women with hypoactive sexual desire disorder (HSDD) report that fibanserin increased their sexual desire and reduced associated distress; http://www.boehringer-ingelheim.com/news/news releases/press releases/2010/19 May 2010; 4 pgs.
Press Release Jun. 17, 2010; Key Facts on HSDD and Flibanserin; http://us.boehringer-ingelheim.com/news events/press releases/press release archive/2010; 2 pgs.
Press Release Jun. 18, 2010; Boehringer Ingelheim comments on Jun. 18th FDA Advisory Committee Meeting; http://us.boehringer-ingelheim.com/news events/press releases; press release archive/2010; 2 pgs.
FDA (U.S. Food and Drug Administration); Transcript of Advisory Committee for Reproductive Health Drugs; Jun. 18, 2010; 293 pgs.

U.S. Appl. No. 08/039,002, filed Jul. 30, 1992, Beitti.
U.S. Appl. No. 11/956,949,filed Dec. 14, 2007, Lewis-D'Agostino, et al.
U.S. Appl. No. 12/280,804, filed Aug. 27, 2008, Ceci.
U.S. Appl. No. 12/306,946, filed Dec. 29, 2008, Becker.
U.S. Appl. No. 12/306,945, filed Dec. 29, 2008, Pyke.
U.S. Appl. No. 12/306,878, filed Dec. 29, 2008, Castrol et al.
U.S. Appl. No. 12/390,665, filed Feb. 23, 2009, Wunderlich et al.
U.S. Appl. No. 12/532,269, filed Dec. 14, 2009, Boeck et al.
U.S. Appl. No. 12/675,231, filed Feb. 25, 2010, Hanes et al.
Alexander et al., J. of Am. Acad. of Nurse Practitioners, 2007, 19:152-163.
Anonymous: "Hormone Patch May Provide Some Increase in Sexual Desire in Menopausal Women" Jul. 25, 2005; URL:http://pubs.ama-assn.org/media/2005a/0725.dtl, 2pgs.
Guilleminault et al., Atypical Sexual Behavior During Sleep, Phychosomatic Med., 2002, 64:328-336.
Basson et al., Sexual psychophysiology and effects of sildenafil citrate in oestrogenised women with acquired genital arousal disorder and impaired orgasm: a randomised controlled trial, BJOG: an International Journal of Obstetrics and Gyn., Nov. 2003, 110:1014-1024.
Basson et al., Efficacy and Safety of Sildenafil Citrate in Women with Sexual Dysfunction Associated with Female Sexual Arousal Disorder, J Women's Health & Gender-Based Medicine, Nov. 4, 2002 11:367-77.
Bechard, et al., Int. J. Pharm., 1992, 87:133-139.
Black et al., Inappropriate sexual behaviors in dementia, J of Geriatric Psychiatry & Neurology, Sep. 2005, 18(3):155 -162.
Braiman, Psychosexual disorders of young adulthood, Clin Obstetrics and Gynecology, 1970, 13(3):734-745.
Buhrich et al., Can fetishism occur in transexuals?, Arch Sex Behav, 1977, 6(3):223-235.
Butts, The relationship between sexual addiction and sexual dysfunction, J. Health Care Underserved, 1992, 3(1):128-35; discussion 136-7.
Buvat et al., Role of hormones in sexual dysfunction, homosexuality, transsexualism, and paraphilia related disorders. Diagnostic and therapeutic consequences, Contracep Fertil Sex, 1996, 24(11):834-846—only English abstract.
Bymaster et al., Fluoxetine, but not other selective serotonin uptake inhibitors, increases norepinephrine and dopamine extracellular levels in prefrontal cortex, Psychopharmacology, 2002, 160:353-361.
Byrn et al., Hydrates & solvates, Solid State Chemistry & Drugs, 1999, Chpt. 11, pp. 233-247.
Chiao et al., Sistemas de liberacion sostenida de drogas, Farmacia Industrial, Chpt. 19, 1988, pp. 2535-2537.
Clayton, Epidemiology and Neurobiology of Femal Sexual Dysfunction, J Sex Med., Nov. 4, 2007, Suppl 4:260-8.
Clayton et al., Burden of phase-specific sexual dysfunction with SSRIs, J Affect Disord., Mar. 2006, 91(1):27-32.
Clayton et al., Prevalence of Sexual Dysfunction Among Newer Antidepressants, J. Clin. Psychiatry, 2002, 63(4):357-366.
CMU Pharmaceutical polymorphism, http://www.andrew.cmu.edu/user/suter/polymorph.html, internet p. 1-3 (2002): obtained Feb. 11, 2009.
Sexual Dysfunction and Hypotestosteronemia in Patients With Obstructive Sleep Apnea Syndrome and Its Effects With CPAP Therapy, http:..clinicaltrials.gov/ct2/show/NCT00832065, obtained Apr. 1, 2009, 4pgs.
Cooper et al., A female sex offender with multiple paraphilias: a psychologic, physiol ogic (laboratory sexual arousal) and endocrine case study, Can J Psychiatry, 1990, 35(4):334-7.
Damour et al., Chemical Abstract, Mar. 29, 1993, 118(13):124537e.
Doelker et al., Crystalline modifications and polymorphism changes during drug manufacturing, Annales Pharmaceutiques Francaises, 2002, 60(3):161-169.
Doelker et al., Physicochemical behavior or active substances. Consequences for the feasibility and stability of pharmaceutical forms, S.T.P. Pharma Pratiques, 1999, 9(5):399-409.
Engleson, Concise Encyclopedia Chemistry, 1993, pp. 872-873.
Giraldi et al., Physiology of Female Sexual Function: Animal Models, J Sex Med, 2004, 1(3):237-253.

Girgis et al., A double-blind trial of clomipramine in premature ejaculation, Andrologia, Jul.-Aug. 1982, 14(4):364-8.
Giron, Thermal analysis and calorimetric methods in the characterisation of polymorphs and solvates, Thermochimica ACTA, 1995, 248:1-59, Elsevier Science.
Grau et al., Risk Factors, Outcome, and Treatment in Subtypes of Ischemic Stroke: The German Stroke Data Bank, Stroke, 2001; 32:2559-2566.
Guarraci et al: Coffee, Tea and Me: Moderate doses of caffeine affect sexual behavior in female rats, Pharma Biochem and Behavior, Nov. 2005, 82(3):522-530. ISSN: 0091-3057 Elsevier, US, abstract.
Goldfischer et al., Selected 2008 Abstracts from the International Society for the Study of Women's Sexual Health, J. Sex. Med., 2008, 5(suppl. 3):159-160.
Goodman, An assessment of clomipramine (Anafranil) in the treatment of premature ejaculation, J Int Med Res., 1980; 8(Suppl 3):53-9.
Haensel et al., Fluoxetine and premature ejaculation: A double-blind, crossover, placebo-controlled study, J Clin Psychopharmacology, 1998, 18:72-77.
Haensel et al., Clomipramine and sexual function in men with premature ejaculation and controls, J Urology, Oct. 1996, 156(B193):1310-1315.
Kafka, A Monoamine Hypothesis for the Pathophysiology of Paraphilic Disorders, Archives of Sex Behav, 1997, 26(4):343-58.
Kandeel et al., Male Sexual Function and its Disorders: Physiology, Pathophysiology, Clinical investigation, and Treatment, Endocrine Reviews, 2001, 22(3):342-388 at 370.
Kennedy et al., Antidepressant-Induced Sexual Dysfunction During Treatment with Moclobemide, Paroxetine, Sertraline, and Venlafaxine, J Clin Psychiatry, 2000; 61:276-81.
Kennedy et al., Sexual dysfunction before antidepressant therapy in major depression, J. Affective Disorders, 1999, 56:201-208.
Konarski et al., Effects of Acute Flibanserin on FDG-PET Brain Glucose Metabolism in Men with Major Depressive Disorder, Aug. 2008 Barcelona meeting of the European College of Nueropsychopharmacology, 3 pgs. (poster—abstract).
Jain et al., Polymorphism in Pharmacy, Indian Drugs, 1986, 23(6):315-329.
Marshall, Unified Approach to the Analysis of Genetic Variation in Serotonergic Pathways, Am. J. Med. Genetics Neurophyschiatric Genetics, 1999, 88:621-627.
McKenna, Neural Circuitry Involved in Sexual Function, J Spinal Cord Med., 2001, 24:148-154.
McMahon et al., Efficacy of type-5 phosphodiesterase inhibitors in the drug treatment of premature ejaculation: a systematic review, BJU Int., 2006, 98:259-72.
Montejo-Gonzales et al., SSRI-induced sexual dysfunction: fluoxetine, paroxetine, sertraline, and fluvoxamine in a prospective, multicenter, and descriptive clinical study of 344 patients, J Sex Marital, 1997 Fall; 23(3):176-94.
Moser, Lust, lack of desire and paraphilias: some thoughts and possible connections, J of Sex & Marital Ther, 1992, 18(1):65-9.
Mutschler et al., the Effect of Drugs: Antidepressive Agents, Manual of Pharmacology and Toxicology, 2001, 8th Ed, pp. 171-172, Scientific Publishing Company PLC, Stuttgart.
Muzaffar et al., J. Pharmacy, 1979, 1(1):59-66.
Nurnberg et al., Sildenafil for Sexual Dysfunction in Women Taking Antidepressants, Am J Psychiatry, October—Letters to the Editor, 1999, 156(10):1664.
Nurnberg et al., Sildenafil Treatment of Women with Antidepressant-Associated Sexual Dysfunction, JAMA, Jul. 2008, 300(4):395-404.
Otsuka, et al., Chem. Pharm. Bull., 1999, 47(6):852.856.
Pharmacopia, 1995, p. 1843.
Porter, Coating of Pharmaceutical Dosage Forms, Remingtons, 1990, Chpt 90, pp. 1666-1675.
Pfaus et al., What can animal models tell us about human sexual response?, Annu Rev Sex Res, 2003, 14:1-63.
Pryor et al., Efficacy and tolerability of dapoxetine in treatment of premature ejaculation: an integrated analysis of two double-blind, randomized controlled trials, Lancet, 2006, 368(9539):929-37.
Pyke et al., Flibanserin: A Novel Centrally Acting Agent that is not an Effective Antidepressant but has Potential to Treat Decreased Sexual Desire in Women, APA, May 2008, 1 pg. (accepted poster).

Pyke et al., Flibanserin: A Novel Centrally Acting Agent that is not an Effective Antidepressant but has Potential to Treat Decreased Sexual Desire in Women, APA, May 2008, 1 pg. (accepted abstract).
Rapkin, General Gynecology, 2007, 196:97-106.
Rendell et al., Sildenafil for Treatment of Erectile Dysfunction in Men with Diabetes, JAMA, 1999, 281:421-426.
Rosen et al., Effects of SSRIs on sexual function: a critical review, J Clin Psychopharmacol., Feb. 1999 19(1):67-85.
Rosen et al., PDE-5 inhibition and sexual response: Pharmacological mechanisms and clinical outcomes, Annual Review of Sex Res, 2002, pp. 36-88.
Rosen, Sexual pharmacology in the 21st century, J Gend Specif Med., Jul.-Aug. 2000, 3(5):45-52.
Rowland, Neurobiology of Sexual Response in Men and Women, 1:CNS Spectr., Aug. 2006, 11(8 Suppl 9):6-12.
Rubenstein, Pharmaceutics: The Science of Dosage Form Design, ed. Aulton, 1988, pp. 304-321, Churchill Livingstone.
Schwartz et al., Conceptual factors in the treatment of paraphilias: a preliminary rep., J of Sex & Marital Ther, 1983, 9(1):3-18.
Semkova et al., Neuroprotective effect of 5-HT1A receptor agonist, Bay ×3702, demonstrated in vitro and in vivo, Euro J Pharm, 1998, 359:251-260.
Martin, Sexsomnia, http://lakesidepress.com/pulmonary/ Sleep/sexsomnia.html, obtianed Apr. 1, 2009, 5pgs.
Singhal, et al., Advanced Drug Delivery Reviews, 2004, 56:335-347.
Soederberg et al., Leptin Is a Risk Marker for First-Ever Hemorrhagic Stroke in a Population-Based Cohort, Stroke, Jl of the Am Heart Assoc., 1999; 30:328-337.
Stearns et al., J. of Clin. Oncology, 2002, 20(6):1436-1438.
Stedman'S Medical Dictionary definition "Prevention," 2000, 28th Ed., 3 pgs., Lippincott Williams & Wilkins.
Stedman'S Medical Dictionary definition "Anxiety", 28$^{th}$ Ed., 2006, p. 114, Lippincott Williams & Wilkins, Baltimore MD.
Stoleru et al., Brain processing of visual sexual stimuli in men with hypoactive sexual desire disorder, Psychiatry Res.: Neuroimaging, 2003, 124(2):67-86.
Thrombolytic Therapy: MedlinePlue Medical Encyclopedia; http://www.nlm.nih.gove/medlineplus/ ency/article/007089.htm accessed Dec. 19, 2009, pp. 1-4.
Vippagunta, Advanced Drug Del. Rev., 2001, 48:3-26.
Welsh et al., Effect of Lactacidosis on Pyridine Nucleotide Stability During Ischemia in Mouse Brain, J Neurochemistry, 1987, 49(3):846-851.
Zverina et al., The occurrence of atypical sexual experience among various femals groups, Arch Sex Behav, 1987, 16(4):321-6.
Clayton et al., Validation of the Decreased Sexual Desire Screener (DSDS): a Brief Diagnostic Instrument for Generalized, Acquired Hypoactive Sexual Desire Disorder in Women, International Society for the Study of Womens Sexual Health (ISSWSH) annual meeting, 2007, 2 pgs. (poster and abstract).
Wunderlich et al., Using e-Diaries to Measure Sexual Desire in Women with Hypoactive Sexual Desire Disorder, International Society for the Study of Womens Sexual Health (ISSWSH) annual meeting, 2007, 11 pgs. (Oral Presentation).
Clayton et al., Validation of the Sexual Interest and Desire Inventory-Female (SIDI-F) in North American Women, International Society for the Study of Womens Sexual Health (ISSWSH) annual meeting, 2007, 3 pgs. (poster and abstract).
Clayton et al., Validity of Sexual Distress Scales vs Electronic Diary in Women with Decreased Sexual Desire , American College of Obstetrics and Gynecologists (ACOG) annual meeting, 2007, 1 pg. (abstract only).
Clayton et al., Validating the Sexual Interest and Desire Inventory (SIDI-F) in North American Women , American College of Obstetrics and Gynecologists (ACOG) annual meeting, 2007, 1 pg. (abstract only).
Clayton et al., Validation of the Sexual Interest and Desire Inventory-Female (SIDI-F) in North American Women, American Psychiatric Association (APA) annual meeting, 2007, 2 pgs. (poster and abstract).
Tignol et al., Using e-Diaries to Measure Sexual Desire in Women with Hypoactive Sexual Desire Disorder, European Society for Sexual Medicine (ESSM) annual meeting, 2007, 9 pgs. (oral presentation).
Clayton, Baseline characteristics of patients enrolled in three Phase III North American trials of flibanserin in premenopausal women with Hypoactive Sexual Desire Disorder, Joint Congress of the European and International Societies of Sexual Medicine (ESSM/ISSM) 2008, 10 pgs. (oral presentation).
Clayton et al., Baseline characteristics of patients enrolled in three Phase III North American trials of flibanserin in premenopausal women with Hypoactive Sexual Desire Disorder, Joint Congress of the European and International Societies of Sexual Medicine (ESSM/ISSM) 2008, 1 pgs. (abstract).
Clayton et al., Baseline characteristics of patients enrolled in three Phase III North American trials of flibanserin in premenopausal women with Hypoactive Sexual Desire Disorder, International Society for the Study of Womens Sexual Health (ISSWSH) annual meeting 2009, poster, 2 pgs. (poster and abstract).
Clayton et al., Validation of the Decreased Sexual Desire Screener (DSDS): A Brief Diagnostic Instrument for Generalized Acquired Female Hypoactive Sexual Desire Disorder (HSDD); J. Sex Med., 2009, pp. 1-9. (epub ahead of print).
Dean, Decreased Sexual Desire Screener © (DSDS ©) for Diagnosis of Hypoactive Sexual Desire Disorder in Women, WONCA Europe conference, 2008, 8 pgs. (oral presentation).
Dean et al., Decreased Sexual Desire Screener © (DSDS ©) for Diagnosis of Hypoactive Sexual Desire Disorder in Women, WONCA Europe conference, 2008, 1 pg. (abstract).
Derogatis et al., Validation of Sexual Distress Scales and Electronic Diary in Women with Hypoactive Sexual Desire Disorder, International Society for the Study of Womens Sexual Health (ISSWSH) annual meeting, 2007, 3 pgs. (poster and abstract).
Derogatis et al., Validation of Sexual Distress Scales and Electronic Diary in Women with Hypoactive Sexual Desire Disorder. American Psychiatric Association (APA) annual meeting, 2007, 2 pgs. (poster and abstract).
Derogatis et al., Content Validity of the Female Sexual Distress Scale-Revised (FSDS-R) in Women with Hypoactive Sexual Desire Disorder (HSDD), Joint Congress of the European and International Societies of Sexual Medicine (ESSM/ISSM) 2008, 5 pgs. (poster, oral presentation and abstract).
Derogatis et al., Validation of the Female Sexual Distress Scale Revised (FSDS-R) for assessing distress in women with Hypoactive Sexual Desire Disorder (HSDD), J Sex Med., 2008, 5:357-364.
Dennerstein et al., Differentiating Four Cognitive-Behavioral Types of Women with Low Sexual Desire, International Society for the Study of Womens Sexual Health (ISSWSH) annual meeting, 2007, 9 pgs. (Oral Presentation).
Dennerstein et al., Differentiating Four Cognitive-Behavioral Types of Women with Decreased Sexual Desire, International Society for the Study of Womens Sexual Health (ISSWSH) annual meeting, 2007, 2 pgs. (abstract).
Dennerstein et al., Differentiating Four Cognitive-Behavioral Types of Women with Decreased Sexual Desire, American Psychiatric Association (APA) annual meeting, 2007, 3 pgs. (poster and abstract).
Dennerstein et al., Differentiating Four Cognitive-Behavioral Types of Women with Decreased Sexual Desire, European Society for Sexual Medicine (ESSM) annual meeting, 2007, 3 pgs. (poster and abstract).
Dennerstein, Differentiating Four Cognitive-Behavioral Types of Women with Low Sexual Desire, European Society for Sexual Medicine (ESSM) annual meeting, 2007, 10 pgs. (oral presentation).
Dennerstein et al., Attitudes Towards Partner Interactions of Women With Characteristics of HSDD: Preliminary Results of a Multinational Study of 1,402 Women. International Society for the Study of Womens Sexual Health (ISSWSH) annual meeting, 2008, 12 pgs. (oral presentation and abstract).

Goldfischer et al., Validation of the Decreased Sexual Desire Screener (DSDS): a Brief Diagnostic Instrument for Generalized, Acquired Hypoactive Sexual Desire Disorder in Women, American Psychiatric Association (APA) annual meeting, 2007, 2 pgs. (poster and abstract).

Pyke et al., The ROSE Study: Placebo-controlled Randomized Withdrawal Trial of Flibanserin for Hypoactive Sexual Desire Disorder in Premenopausal Women, Sexual Medicine Society of North America (SMSNA) annual meeting, 2007, 1 pg. (poster).

Goldfischer et al., Efficacy of Continued Flibanserin Treatment on Sexual Desire and Satisfying Sexual Events in Premenopausal Women With HSDD: Results From the ROSE Study, International Society for the Study of Womens Sexual Health (ISSWSH) annual meeting, 2008, 1 pgs. (abstract).

Goldfischer et al., Efficacy of Continued Flibanserin Treatment on Distress Associated with Sexual Dysfunction in Premenopausal Women With HSDD: Results From the ROSE Study, International Society for the Study of Womens Sexual Health (ISSWSH) annual meeting, 2008, 2 pgs. (poster and abstract).

Goldfischer et al., Efficacy of Continued Flibanserin Treatment on Sexual Functioning in Premenopausal Women With HSDD: Results From the ROSE Study, International Society for the Study of Womens Sexual Health (ISSWSH) annual meeting, 2008, oral presentation, 1 pg. (abstract only).

Goldfischer et al., The ROSE Study: Placebo-controlled Randomized Withdrawal Trial of Flibanserin for Hypoactive Sexual Desire Disorder in Premenopausal Women, European Board and College of Obstetrics and Gynaecology (EBCOG) annual meeting, 2008, 1 pg. (abstract only).

Goldfischer et al., The ROSE Study: Placebo-controlled Randomized Withdrawal Trial of Flibanserin for Hypoactive Sexual Desire Disorder in Premenopausal Women. European Federation of Sexology (EFS), 2008, 7 pgs. (oral presentation and abstract).

Goldfischer et al., Decreased Sexual Desire Screener (DSDS) for Diagnosis of Hypoactive Sexual Desire Disorder in Women, American College of Obstetrics and Gynecologists (ACOG) annual meeting, 2008, 2 pgs. (poster and abstract).

Goldfischer et al., Efficacy of Continued Flibanserin Treatment in Premenopausal Women with Hypoactive Sexual Desire Disorder: Results from the ROSE Study, International Academy of Sex Research (IASR) annual meeting, 2008, 3 pgs. (poster and abstract).

Goldfischer et al., Safety and Tolerability of Flibanserin in Premenopausal Women with Hypoactive Sexual Desire Disorder: Results from the ROSE Study, International Academy of Sex Research (IASR) annual meeting, 2008, 3 pgs. (poster and abstract).

Goldfischer et al., Efficacy and Safety of Flibanserin in Premenopausal Women with Hypoactive Sexual Desire Disorder: Results from the Randomized Withdrawal ROSE Study, Institute on Psychiatric Services (IPS) annual meeting, 2008, 2 pgs. (poster and abstract).

Goldfischer et al., Decreased Sexual Desire Screener (DSDS) for Diagnosis of Hypoactive Sexual Desire Disorder in Women, Sexual Medicine Society of North America (SMSNA) annual meeting, 2008, 3 pgs. (poster and abstract).

Goldfischer et al., Efficacy and Safety of Flibanserin in Premenopausal Women with Hypoactive Sexual Desire Disorder: Results From the Randomized Withdrawal ROSE Study, Sexual Medicine Society of North America (SMSNA) annual meeting, 2008, 3 pgs. (poster and abstract).

Goldfischer, Efficacy of Continued Flibanserin Treatment in Premenopausal Women with Hypoactive Sexual Desire Disorder: Results From the ROSE Study, Joint Congress of the European and International Societies of Sexual Medicine (ESSM/ISSM), 2008, 10 pgs. (oral presentation).

Goldfischer et al., Efficacy of Continued Flibanserin Treatment in Premenopausal Women with Hypoactive Sexual Desire Disorder: Results From the ROSE Study, Joint Congress of the European and International Societies of Sexual Medicine (ESSM/ISSM), 2008, 2 pgs. (abstract).

Goldfischer et al., Safety and Tolerability of Continued Flibanserin Treatment in Premenopausal Women with Hypoactive Sexual Desire Disorder: Results From the ROSE Study, Joint Congress of the European and International Societies of Sexual Medicine (ESSM/ISSM), 2008, 2 pgs. (poster and abstract).

Goldstein et al., Differences in Patient-Physician Communication Regarding Hypoactive Sexual Desire Disorder (HSDD) , Sexual Medicine Society of North America (SMSNA) annual meeting, 2007, 3 pgs. (poster and abstract).

Goldstein et al., Emotions Related to Distress in Patients with Hypoactive Sexual Desire Disorder: Results of Patient and Physician Interviews, Sexual Medicine Society of North America (SMSNA) annual meeting, 2007, 3 pgs. (poster and abstract).

Jolly et al., Design of Phase III Pivotal Trials of Flibanserin in Female Hypoactive Sexual Desire Disorder (HSDD), European Federation of Sexology (EFS), 2008, 2 pgs. (poster and abstract).

Nappi et al., Validation of the Sexual Interest and Desire Inventory-Female (SIDI-F) in European Women, European Federation of Sexology (EFS), 2008, 2 pgs. (poster and abstract).

Nappi, Decreased Sexual Desire Screener (DSDS) for Diagnosis of Hypoactive Sexual Desire Disorder (HSDD) in European Women, Joint Congress of the European and International Societies of Sexual Medicine (ESSM/ISSM), 2008, 8 pgs. (oral presentation).

Nappi et al., Decreased Sexual Desire Screener (DSDS) for Diagnosis of Hypoactive Sexual Desire Disorder (HSDD) in European Women, Joint Congress of the European and International Societies of Sexual Medicine (ESSM/ISSM), 2008, 1 pg. (abstract).

Nappi et al., Decreased Sexual Desire Screener (DSDS) for Diagnosis of Hypoactive Sexual Desire Disorder (HSDD) in European Women, International Society for the Study of Womens Sexual Health (ISSWSH) annual meeting, 2009, oral presentation, 8 pgs. (oral presentation).

Nappi et al., Decreased Sexual Desire Screener (DSDS) for Diagnosis of Hypoactive Sexual Desire Disorder (HSDD) in European Women, International Society for the Study of Womens Sexual Health (ISSWSH) annual meeting, 2009, oral presentation, 1 pg. (abstract).

Pyke et al., Using e-Diaries to Measure Sexual Desire in Women with Hypoactive Sexual Desire Disorder, American Psychiatric Association (APA) annual meeting, 2007, 2 pgs. (poster and abstract).

Pyke et al., The ROSE Study: Placebo-Controlled Randomized Withdrawal Trial of Flibanserin for Hypoactive Sexual Desire Disorder in Premenopausal Women (Study Design Only), Institute on Psychiatric Services (IPS) annual meeting, 2007, 2 pgs. (poster and abstract).

Pyke et al., Safety and Tolerability of Flibanserin in Premenopausal Women With Hypoactive Sexual Desire Disorder (HSDD): Results From the Rose Study, American Psychiatric Association (APA) annual meeting, 2008, 2 pgs. (poster and abstract).

Pyke et al., Flibanserin: a Novel Centrally Acting Agent That is not an Effective Antidepressant but has Potential to Treat Decreased Sexual Desire in Women, American Psychiatric Association (APA) annual meeting, 2008, 2 pgs. (poster and abstract).

Rosen et al., The Predictors of Sexual Distress in Women With Low Sexual Desire, International Society for the Study of Womens Sexual Health (ISSWSH) annual meeting, 2009, oral presentation, 15 pgs. (oral presentation and abstract).

Shifren et al., Sexual Problems and Distress in United States Women: Prevalence and Correlates , Obstet. Gynecology, Nov. 2008, 112(5):970-978.

Shifren et al., Treatment-seeking Behavior of U.S. Women with Hypoactive Sexual Desire Disorder (HSDD), American College of Obstetrics and Gynecologists (ACOG) annual meeting, 2008, 2 pgs. (poster and abstract).

Pyke et al., Validation of the Sexual Interest and Desire Inventory-Female (SIDI-F) in European Women, International Society for the Study of Womens Sexual Health (ISSWSH) annual meeting, 2007, 20 pgs. (oral presentation).

Nappi et al., Validation of the Sexual Interest and Desire Inventory-Female (SIDI-F) in European Women, European Society for Sexual Medicine (ESSM) annual meeting, 2007, 19 pgs. (oral presentation).

Sand et al., The Female Sexual Function Index (FSFI): A Potential "Gold Standard" Measure for Assessing Therapeutically-Induced Change in Female Sexual Function, ASRM, 2009, Oct. 17-21, 2009, Atlanta, Georgia, 2 pgs. (poster and abstract).

Smith et al., Pharmacokinetics of Flibanserin in Premenopausal Women With Hypoactive Sexual Desire Disorder Including Effects on the Female Sexual Function Index, ESSM, 2009, Nov. 2009, 2 pgs., Lyon. (poster and abstract).

Clayton et al., Efficacy of Flibanserin As a Potential Treatment for Hypoactive Sexual Desire Disorder in North American Premenopausal Women: Results From the Dahlia Trial, ESSM, 2009, Nov. 2009, 2 pgs., Lyon. (poster and abstract).

Thorp et al., Efficacy of Flibanserin As a Potential Treatment for Hypoactive Sexual Desire Disorder in North American Premenopausal Women: Results From the Daisy Trial, ESSM, 2009, Nov. 2009, 3 pgs., Lyon. (poster and abstract).

Jolly et al., Design of Randomized Controlled Trials of Flibanserin in Premenopausal Women With Hypoactive Sexual Desire Disorder, ESSM 2009, Nov. 2009, 3 pgs., Lyon. (poster and abstract).

Revicki et al., Content Validity of the Female Sexual Function Index in Pre- and Postmenopausal Women With Hypoactive Sexual Desire Disorder, ESSM 2009, Nov. 2009, 2 pgs., Lyon. (poster and abstract).

Aubert et al., Comparison of Flibanserin With the 5-Htla Agonist (+)-8-Oh-Dpat in Affecting Interactions Between Male-Female Marmoset Pairs, ESSM 2009, Nov. 2009, 2 pgs., Lyon (poster and abstract).

Rosen et al., Criterion Validity of the Sexual Desire Domain of the Female Sexual Function Index (Fsfi): Identifying a Diagnostic Cut-Point for Differentiating Women With and Without HSDD, ESSM 2009, Nov. 2009, 3 pgs., Lyon. (poster and abstract).

Rosen et al., Validation of the FSFI Sexual Desire Domain Diagnostic Cut-Point in Predicting Hsdd in Women: Independent Replication and Confirmation, ESSM 2009, Nov. 2009, 2 pgs., Lyon. (poster and abstract).

Nappi, Efficacy of Flibanserin As a Potential Treatment for Hypoactive Sexual Desire Disorder in European Premenopausal Women: Results From the Orchid Trial; ESSM 2009, Nov. 2009, 12 pgs., Lyon. (oral presentation).

Nappi et al., Efficacy of Flibanserin As a Potential Treatment for Hypoactive Sexual Desire Disorder in European Premenopausal Women: Results From the Orchid Trial; ESSM 2009, Nov. 2009, 1 pg., Lyon. (abstract).

Holstege et al., Differences in Brain Activity in Premenopausal Women With Hypoactive Sexual Desire Disorder (Hsdd) Compared to Women Without Sexual Dysfunction, ESSM 2009, Nov. 2009, 2 pgs., Lyon. (abstract only).

Holstege et al., Brain activation and de-activation caused by erotic movies is lower in HSDD—than in non-HSDD volunteers, ESSM 2009, 8 pgs. (oral presentation).

Jolly, Efficacy of Flibanserin 100 Mg Qhs As a Potential Treatment for Hypoactive Sexual Desire Disorder in Premenopausal Women, ESSM 2009, Nov. 2009, 12 pgs., Lyon. (oral presentation).

Jolly et al., Efficacy of Flibanserin 100 Mg Qhs As a Potential Treatment for Hypoactive Sexual Desire Disorder in Premenopausal Women, ESSM 2009, Nov. 2009, 1 pgs., Lyon. (abstract).

Jolly et al., Efficacy of Flibanserin 100 Mg Qhs As a Potential Treatment for Hypoactive Sexual Desire Disorder in North American Premenopausal Women, ESSM 2009, Nov. 2009, 2 pgs., Lyon. (poster and abstract).

Clayton, Safety and Tolerability of Flibanserin in Premenopausal Women With Hypoactive Sexual Desire Disorder, ESSM 2009, Nov. 2009, 12 pgs., Lyon. (oral presentation).

Jolly et al., Safety and Tolerability of Flibanserin in Premenopausal Women With Hypoactive Sexual Desire Disorder, ESSM 2009, Nov. 2009, 1 pg., Lyon. (abstract).

Jolly et al., Efficacy of Flibanserin As a Potential Treatment for Hypoactive Sexual Desire Disorder in North American Premenopausal Women: Results From the Violet Trial, ESSM 2009, Nov. 2009, 3 pgs., Lyon. (poster and abstract).

Fuchs, Baseline Characteristics of Patients Enrolled in Three Phase III North American Trials of Flibanserin in Premenopausal Women With Hypoactive Sexual Desire Disorder, FIGO 2009, Oct. 2009, 10 pgs., Cape Town, South Africa. (oral presentation).

Goldfischer, Efficacy and Safety of Flibanserin in a Randomized Withdrawal Study of Premenopausal Women With Hypoactive Sexual Desire Disorder, FIGO2009, Oct. 2009, 12 pgs., Cape Town, South Africa. (oral presentation).

Goldfischer et al., Efficacy and Safety of Flibanserin in a Randomized Withdrawal Study of Premenopausal Women With Hypoactive Sexual Desire Disorder, FIGO2009, Oct. 2009, 1 pgs., Cape Town, South Africa. (abstract).

Revicki et al., Content Validity of the Female Sexual Function Index in Pre- and Postmenopausal Women With Hypoactive Sexual Desire Disorder, ICSM 2009, Jul. 2009, 2 pgs., Paris. (poster and abstract).

Revicki et al., Content Validity of the Female Sexual Function Index in Pre-Menopausal Women With Hypoactive Sexual Desire Disorder, ICSM 2009, Jul. 2009, 2 pgs., Paris. (poster and abstract).

Rosen et al., Criterion Validity of the Sexual Desire Domain of the Female Sexual Function Index (Fsfi): Identifying a Diagnostic Cut-Point for Differentiating Women With and Without Hsdd, ICSM 2009, Jul. 2009, 2 pgs., Paris. (poster and abstract).

Rosen et al., Validation of the Fsfi Sexual Desire Domain Diagnostic Cut-Point in Predicting Hsdd: Independent Replication and Confirmation, ICSM 2009, Jul. 2009, 2 pgs., Paris. (poster and abstract).

Sand et al., The Female Sexual Function Index (Fsfi): A Potential "Gold Standard" Measure for Assessing Sexual Function in Women, ICSM 2009, Jul. 2009, 2 pgs., Paris. (poster and abstract).

Jayne, Results From the Dahlia (511.70) Trial: A Prospective Study of Flibanserin for the Treatment of Hypoactive Sexual Desire Disorder in North American Premenopausal Women, SMSNA 2009, Nov. 2009, 3 pgs San Diego, USA (oral presentation).

Jayne et al., Results From the Dahlia (511.70) Trial: A Prospective Study of Flibanserin for the Treatment of Hypoactive Sexual Desire Disorder in North American Premenopausal Women, SMSNA 2009, Nov. 2009, 2 pgs., San Diego, USA (abstract and poster).

Sand et al., Efficacy of Flibanserin in North American Premenopausal Women With Hypoactive Sexual Desire Disorder: Results From the Daisy Trial, SMSNA 2009, Nov. 2009, 2 pgs., San Diego, USA. (poster and abstract).

Sand, Efficacy of Flibanserin in North American Premenopausal Women With Hypoactive Sexual Desire Disorder: Results From the Daisy Trial, SMSNA 2009, Nov. 2009, 2 pgs., San Diego, USA. (oral presentation).

Sand et al., The Female Sexual Function Index (Fsfi) Is a Potential "Gold Standard" Measure for Assessing Sexual Function in Pre- and Post-Menopausal Women: A Systematic Review, SMSNA 2009, Nov. 2009, 2 pgs., San Diego, USA. (poster and abstract).

Sand et al., Efficacy of Flibanserin 100 Mg Qhs As a Potential Treatment for Hypoactive Sexual Desire Disorder in North American Premenopausal Women, SMSNA 2009, Nov. 2009, 2 pgs., San Diego, USA. (poster and abstract).

Sand, Efficacy of Flibanserin 100 Mg Qhs As a Potential Treatment for Hypoactive Sexual Desire Disorder in North American Premenopausal Women, SMSNA 2009, Nov. 2009, 2 pgs., San Diego, USA. (oral presentation).

Holstege et al., Differences in Brain Activity in Premenopausal Women With Hypoactive Sexual Desire Disorder (Hsdd) Compared to Women Without Sexual Dysfunction, SMSNA 2009, Nov. 2009, 2 pgs., San Diego, USA (abstract only).

Holstege et al., Brain activation and de-activation caused by erotic movies is lower in Hsdd—than in non-HSDD volunteers, SMSNA, 2009, 4 pgs (poster & oral presentation).

Sand et al., Pooled Clinical Trail Analysis of Flibanserin Safety and Tolerability in Premenopausal Women with Hypoactive Sexual Desire Disorder, SMSNA, 2009, 2 pgs. (poster and abstract).

Sand, Pooled Clinical Trail Analysis of Flibanserin Safety and Tolerability in Premenopausal Women with Hypoactive Sexual Desire Disorder, SMSNA, 2009, 2 pgs. (oral presentation).

Sand et al., Effacacy of Flibanserin in North American Premenopausal Women with Hypoactive Sexual Desire Disorder: Results from the Violet Trial, SMSNA, 2009, 3 pgs. (poster and abstract).

Sand, Effacacy of Flibanserin in North American Premenopausal Women with Hypoactive Sexual Desire Disorder: Results from the Violet Trial, SMSNA, 2009, 2 pgs. (oral presentation).

Meston, The Female Sexual Function Index (FSFI) is a Potential "Gold Standard" Measure for Assessing Sexual Function in Pre- and post-menopausal Women: a Systematic Review, SMSNA, 2009, 3 pgs. (oral presentation).

Goldfischer, Efficacy and Safety of Flibanserin in a Randomized Withdrawal Study of Premenopausal Women With Hypoactive Sexual Desire Disorder, WAS, 2009, 12 pgs. (oral presentation).
Goldfischer et al., Efficacy and Safety of Flibanserin in a Randomized Withdrawal Study of Premenopausal Women With Hypoactive Sexual Desire Disorder, WAS, 2009, 1 pgs. (abst.).
Clayton et al., Baseline Characteristics of Patients Enrolled in Three Phase III North American Trials of Flibanserin in Premenopausaul Women with Hypoactive Sexual Desire Disorder, WAS, 2009, 2 pgs. (poster and abstract).
Clayton, Baseline Characteristics of Patients Enrolled in Three Phase III North American Trials of Flibanserin in Premenopausaul Women with Hypoactive Sexual Desire Disorder, WAS, 2009, 4 pgs. (oral presentation).
Derogatis et al., Content Validity of the Female Sexual Distress Scale-Revised in Women With Hypoactive Sexual Desire Disorder, WAS, 2009, 1 pg. (abstract only).
Dennerstein et al., Attitudes Toward and Frequency of Partner Interactions Among Women Reporting Decreased Sexual Desire, J. Sex Med., 2009, 6:1668-1673.
Goldstein et al., National Differences in Patient-Clinician Communication Regarding Hypoactive Sexual Desire Disorder, J. Sex Med., 2009, 6:1349-1357.
Johannes et al., Distressing Sexual Problems in United States Women Revisited: Prevalence After Accounting for Depression, J. Clin. Psych., 2009, 70(12):1698-1706.
Pfaus, Pathways of Sexual Desire, J. Sex Med., 2009, 6:1506-1533.
Rosen et al., Correlates of Sexually Related Personal Distress in Women with Low Sexual Desire, J. Sex Med., 2009, 6:1549-1560.
Lewis-D' Agostino et al., Validating the Sexual Interest and Desire Inventory (SIDI-F) in North American Women, American College of Obstetrics and Gynecologists (ACOG) annual meeting, 2007, 1 pg. (poster).
Shifren et al., Help-Seeking Behavior of Women with Self-Reported Distressing Sexual Problems, J. of Women's Health, 2009, 18(4):461-468.
Wunderlich et al., Validity of Sexual Distress Scales vs Electronic Diary in Women with Decreased Sexual Desire, American College of Obstetrics and Gynecologists (ACOG) annual meeting, 2007, 1 pg. (poster).
Clayton et al., Using e-Diaries to Measure Sexual Desire in Women with Hypoactive Sexual Desire Disorder, European Society for Sexual Medicine (ESSM) annual meeting, 2007, 2 pgs. (abstract).
Van Lunsen et al., Validation of the Sexual Interest and Desire Inventory-Female (SIDI-F) in European Women, European Society for Sexual Medicine (ESSM) annual meeting, 2007, 1 pg. (abstract).
Clayton et al., Using e-Diaries to Measure Sexual Desire in Women with Hypoactive Sexual Desire Disorder, International Society for the Study of Womens Sexual Health (ISSWSH) annual meeting, 2007, 2 pgs. (abstract).
Van Lundsen, Validation of the Sexual Interest and Desire Inventory-Female (SIDI-F) in European women, ISSWSH, 2007, 2 pgs. (abstract).
Goldfischer et al., The ROSE Study: Placebo-controlled Randomized Withdrawal Trial of Flibanserin for Hypoactive Sexual Desire Disorder in Premenopausal Women, Sexual Medicine Society of North America (SMSNA) annual meeting, 2007, 1 pg. (abstract).
Krychman et al., The ROSE Study: Placebo-controlled Randomized Withdrawal Trial of Flibanserin for Hypoactive Sexual Desire Disorder in Premenopausal Women, European Board and College of Obstetrics and Gynaecology (EBCOG) annual meeting, 2008, 6 pgs. (poster and oral presentation).
Clayton et al., Baseline Characteristics of Patients Enrolled in Three Phase III North American Trials of Flibanserin in Premenopausal Women With Hypoactive Sexual Desire Disorder, FIGO 2009, Oct. 2009, 1 pg., Cape Town, South Africa. (abstract).
Scandroglio et al., Ex Vivo binding of Flibanserin to Serotonin-5-HT1A and 5-HT2A Receptors, Pharm. Res., 2001, 43(2):179-183.
D'Aquila et al., Anti-anhedonic actions of the novel serotonergic agent flibanserin, a potential rapidly-acting antidepressant, Euro. J. Pharm., 1997, 340:121-132.
Flik et al., Assessment of serotonin and catecholamine levels in the female rat brain following acute and chronic administration with flibanserin, a potential novel treatment for hypoactive sexual desire disorder: An in vivo microdialysis study, presented at Neuroscience 2009, Feb. 3, 2010, http://www.abstractsonline.com/Plan/AbstractPrintView.aspx?mID=2285&sKey=65206..., 2 pgs.
Banfi et al., Benzimidazolone Derivatives: a new class of putative antidepressant agents, 13th Int. Symp. on Medicinal Chemistry, Sep. 19-23, 1994, p. 102. (abstract).
Borsini et la., BIMT 17, a 5-HT1A receptor agonist/5-HT2A receptor antagonist, directly activates portsynaptic 5-HT inhibitory responses in the rat cerebral cortex, Naunyn-Schmiedeberg's Arch Pharm., 1995, 352:283-290.
Boehringer Ingelheim, Flibanserin BIMT-17, Drugs of the Future, 1999, 24(1):91.
Podhorna et al., Flibanserin has anxiolytic effects without locomotor side effects in the infant rat ultrasonic vocalization model of anxiety, Workshop on Depression Anxiety Spectrum Disorders: from Neurobiology to Novel Pharm. Treatmts, Int. Acad. for Biomed. and Drug Res., Abstract—Book, Milan, Sep. 6-7, 2000, 1 pg.
Vaccarino et al., Flibanserin, a 5-HT1A agonist/5-HT2A antagonist, decreases sucrose intake in operant and non-operant paradigms in rats, Soc. Neurosci. Abstr., 2000, 26:394:Abstr 144.9, 30th Ann. Mtg. of Soc. For Neurosci, New Orleans, Nov. 4-9, 1000, 1 pg.
Borsini et al., Further characterisation of potential antidepressant action of flibanserin, Psychopharm., 2001, 159:64-69.
Rueter et al., In Vivo Electrophysiological Assessment of the Agonistic Properties of Flibanserin at Pre- and Postsynaptic 5-HT1A Receptors in the Rat Brain, Synapse, 1998, 29:392-405.
Cervo et al., Involvement of 5-HT1A receptors in flibanserin discriminative stimulus in female rats, Neurosci 2009, Feb. 3, 2010, http://www.abstractsonline.com/Plan/AbstratPrintView.aspx?mID=2285&sKey=65206..., 2pgs.
Cervo et al., Involvement of 5-HT1A receptors in flibanserin discriminative stimulus in female rats, Dept. CNS Diseases, Prog. No. 465.20, 2009 Neurosci., Oct. 19, 2009, 1 pg. (poster).
Ferger et al., Neurochemical characterization of Flibanserin a phase III drug for treatment of hypoactive sexual desire disorder (HSDD) in women, Neurosci 2009, Feb. 3, 2010, http://www.abstractsonline.com/Plan/AbstractPrintView.aspx?mIK=2285&sKey=65206..., 2pgs.
Flik et al., Assessment of serotonin and catecholamine levels in the female rat brain following acute and chronic administration with flibanserin, a potential novel treatment for hypoactive sexual desire disorder: an in vivo microdialysis study, SFN, 2009, 1 pg. (poster).
Ferger et al., Neurochemical characterization of Flibanserin a phase III drug for treatment of hypoactive sexual desire disorder (HSDD) in women, SFN, 2009, 1 pg. (poster).
Evans et al., The Effects of Flibanserin on Amphetamine Withdrawal-Induced hypolocomotion in Rats, Soc. Neurosci Abstr., Nov. 7-12, 1998, 24:2133:Abstr 848.5, 28th Ann. Mtg. of the Soc. For Neurosci, Los Angeles, 1 pg.
Advisory Action dated Dec. 27, 2005, U.S. Appl. No. 10/272,603, filed Oct. 16, 2002 now US Pat. No. 7151103, issued Dec. 19, 2006, 3 pgs.
Examiner's Interview dated Jun. 23, 2006, U.S. Appl. No. 10/272,603, filed Oct. 16, 2002 now US Pat. No. 7151103, issued Dec. 19, 2006, 2 pgs.
Examiner's Interview dated Oct. 20, 2005, U.S. Appl. No. 10/272,603, filed Oct. 16, 2002 now US Pat. No. 7151103, issued Dec. 19, 2006, 1 pg.
Final Office Action dated Jun. 2, 2005, U.S. Appl. No. 10/272,603, filed Oct. 16, 2002 now US Pat. No. 7151103, issued Dec. 19, 2006, 9 pgs.
Notice of Allowance dated Jun. 23, 2006, U.S. Appl. No. 10/272,603, filed Oct. 16, 2002 now US Pat. No. 7151103, issued Dec. 19, 2006, 7 pgs.
Notice of Appeal/Amendment dated Nov. 8, 2005, U.S. Appl. No. 10/272,603, filed Oct. 16, 2002 now US Pat. No. 7151103, issued Dec. 19, 2006, 9 pgs.
Office Action dated Oct. 14, 2004, U.S. Appl. No. 10/272,603, filed Oct. 16, 2002 now US Pat. No. 7151103, issued Dec. 19, 2006, 8 pgs.
RCE/Supp. Amendment dated Jun. 8, 2006, U.S. Appl. No. 10/272,603, filed Oct. 16, 2002 now US Pat. No. 7151103, issued Dec. 19, 2006, 29 pgs.

Reply dated Feb. 14, 2005, U.S. Appl. No. 10/272,603, filed Oct. 16, 2002 now US Pat. No. 7151103, issued Dec. 19, 2006, 20 pgs.
Examiner's Search Strategy dated Jun. 20, 2006, U.S. Appl. No. 10/272,603, filed Oct. 16, 2002 now US Pat. No. 7151103, issued Dec. 19, 2006, 2 pgs.
Examiner's Search Strategy dated Jun. 21, 2006, U.S. Appl. No. 10/272,603, filed Oct. 16, 2002 now US Pat. No. 7151103, issued Dec. 19, 2006, 20 pgs.
Examiner's Search Strategy dated Sep. 22, 2004, U.S. Appl. No. 10/272,603, filed Oct. 16, 2002 now US Pat. No. 7151103, issued Dec. 19, 2006, 83 pgs.
Examiner's Search Strategy dated Sep. 28, 2004, U.S. Appl. No. 10/272,603, filed Oct. 16, 2002 now US Pat. No. 7151103, issued Dec. 19, 2006, 117 pgs.
Examiner's Search Strategy dated Sep. 29, 2004, U.S. Appl. No. 10/272,603, filed Oct. 16, 2002 now US Pat. No. 7151103, issued Dec. 19, 2006, 1 pg.
Examiner's Search Strategy dated Oct. 14, 2004, U.S. Appl. No. 10/272,603, filed Oct. 16, 2002 now US Pat. No. 7151103, issued Dec. 19, 2006, 3pgs.
Final Office Action dated Oct. 5, 2005, U.S. Appl. No. 10/210,474, filed Aug. 1, 2002 now US Pat. No. 7183410, issued Feb. 27, 2007, 6 pgs.
Notice of Allowance dated Jan. 30, 2006, U.S. Appl. No. 10/210,474, filed Aug. 1, 2002 now US Pat. No. 7183410, issued Feb. 27, 2007, 7 pgs.
Notice of Allowance dated Jul. 12, 2006, U.S. Appl. No. 10/210,474, filed Aug. 1, 2002 now US Pat. No. 7183410, issued Feb. 27, 2007, 7 pgs.
Office Action dated Mar. 16, 2005, U.S. Appl. No. 10/210,474, filed Aug. 1, 2002 now US Pat. No. 7183410, issued Feb. 27, 2007, 9 pgs.
Office Action dated Jul. 26, 2004, U.S. Appl. No. 10/210,474, filed Aug. 1, 2002 now US Pat. No. 7183410, issued Feb. 27, 2007, 7 pgs.
Response to Final Office Action dated Dec. 15, 2005, U.S. Appl. No. 10/210,474, filed Aug. 1, 2002 now US Pat. No. 7183410, issued Feb. 27, 2007, 9 pgs.
Reply dated Jan. 26, 2005, U.S. Appl. No. 10/210,474, filed Aug. 1, 2002 now US Pat. No. 7183410, issued Feb. 27, 2007, 24 pgs.
Amendment dated Jul. 11, 2005, U.S. Appl. No. 10/210,474, filed Aug. 1, 2002 now US Pat. No. 7183410, issued Feb. 27, 2007, 13 pgs.
Examiner's Search Strategy dated Mar. 10, 2005, U.S. Appl. No. 10/210,474, filed Aug. 1, 2002 now US Pat. No. 7183410, issued Feb. 27, 2007, 36 pgs.
Examiner's Search Strategy dated Sep. 30, 2005, U.S. Appl. No. 10/210,474, filed Aug. 1, 2002 now US Pat. No. 7183410, issued Feb. 27, 2007, 6 pgs.
Reply with Amendment dated Mar. 8, 2005, U.S. Appl. No. 10/210,474, filed Aug. 1, 2002 now US Pat. No. 7183410, issued Feb. 27, 2007, 10 pgs.
Supplemental Amendment dated Jan. 19, 2006, U.S. Appl. No. 10/210,474, filed Aug. 1, 2002 now US Pat. No. 7183410, issued Feb. 27, 2007, 6 pgs.
Examiner's Interview dated Nov. 19, 2007, U.S. Appl. No. 11/546,303, filed Oct. 12, 2006, 3 pgs.
Final Office Action dated Sep. 14, 2007, U.S. Appl. No. 11/546,303, filed Oct. 12, 2006, 4 pgs.
Office Action dated Jan. 5, 2007, U.S. Appl. No. 11/546,303, filed Oct. 12, 2006, 7 pgs.
Response dated Jul. 5, 2007, U.S. Appl. No. 11/546,303, filed Oct. 12, 2006, 6 pgs.
Examiner's Search Strategy dated Mar. 10, 2005, U.S. Appl. No. 11/546,303, filed Oct. 12, 2006, 36 pgs.
Examiner's Interview Summ. Dated Jan. 17, 2008, U.S. Appl. No. 11/546,304, filed Oct. 12, 2006 now US Pat No. 7420057 issued Sep. 2, 2008, 3 pgs.
Notice of Allowance dated Apr. 30, 2008, U.S. Appl. No. 11/546,304, filed Oct. 12, 2006 now US Pat No. 7420057 issued Sep. 2, 2008, 8 pgs.
Office Action dated Jan. 3, 2007, U.S. Appl. No. 11/546,304, filed Oct. 12, 2006 now US Pat No. 7420057 issued Sep. 2, 2008, 7 pgs.
Office Action dated Jul. 18, 2007, U.S. Appl. No. 11/546,304, filed Oct. 12, 2006 now US Pat No. 7420057 issued Sep. 2, 2008, 4 pgs.
Response dated Jan. 17, 2008, U.S. Appl. No. 11/546,304, filed Oct. 12, 2006 now US Pat No. 7420057 issued Sep. 2, 2008, 24 pgs.
Response dated Apr. 3, 2007, U.S. Appl. No. 11/546,304, filed Oct. 12, 2006 now US Pat No. 7420057 issued Sep. 2, 2008, 7 pgs.
Supp. Response dated Mar. 19, 2008, U.S. Appl. No. 11/546,304, filed Oct. 12, 2006 now US Pat No. 7420057 issued Sep. 2, 2008, 13 pgs.
Supp. Response dated Mar. 24, 2008, U.S. Appl. No. 11/546,304, filed Oct. 12, 2006 now US Pat No. 7420057 issued Sep. 2, 2008, 14 pgs.
2nd Supp. Response dated Apr. 23, 2008, U.S. Appl. No. 11/546,304, filed Oct. 12, 2006 now US Pat No. 7420057 issued Sep. 2, 2008, 14 pgs.
Final Office Action dated Apr. 23, 2007, U.S. Appl. No. 11/079,070, filed Mar. 14, 2005, 11 pgs.
Notice of Allowance dated Sep. 14, 2007, U.S. Appl. No. 11/079,070, filed Mar. 14, 2005, 6 pgs.
Office Action dated Jan. 11, 2008, U.S. Appl. No. 11/079,070, filed Mar. 14, 2005, 8 pgs.
Office Action dated Sep. 13, 2006, U.S. Appl. No. 11/079,070, filed Mar. 14, 2005, 5 pgs.
Response to Final Office Action dated Jul. 23, 2007, U.S. Appl. No. 11/079,070, filed Mar. 14, 2005, 7 pgs.
RCE dated Nov. 2, 2007, U.S. Appl. No. 11/079,070, filed Mar. 14, 2005, 4 pgs.
Response dated Jan. 16, 2007, U.S. Appl. No. 11/079,070, filed Mar. 14, 2005, 8 pgs.
Examiner Search Strategy dated Jan. 3, 2008, U.S. Appl. No. 11/079,070, filed Mar. 14, 2005, 20 pgs.
Examiner's Search Strategy dated Jul. 21, 2006, U.S. Appl. No. 11/079,070, filed Mar. 14, 2005, 106 pgs.
Advisory Action dated Jul. 2, 2009, U.S. Appl. No. 11/278,551, filed Apr. 4, 2006, 3 pgs.
Final Office Action dated Apr. 13, 2009, U.S. Appl. No. 11/278,551, filed Apr. 4, 2006, 9 pgs.
Office Action dated Jun. 1, 2007, U.S. Appl. No. 11/278,551, filed Apr. 4, 2006, 9 pgs.
Office Action dated Jul. 6, 2006, U.S. Appl. No. 11/278,551, filed Apr. 4, 2006, 8 pgs.
Office Action dated Jul. 9, 2008, U.S. Appl. No. 11/278,551, filed Apr. 4, 2006, 12 pgs.
Office Action dated Dec. 28, 2009, U.S. Appl. No. 11/278,551, filed Apr. 4, 2006, 9 pgs.
Responsive Amendment to Final Office Action, dated Jun. 12, 2009, U.S. Appl. No. 11/278,551, filed Apr. 4, 2006, 63 pgs.
RCE and Responsive Amendment to Final Office Action, dated Oct. 7, 2009, U.S. Appl. No. 11/278,551, filed Apr. 4, 2006, 14 pgs.
Response dated Jan. 9, 2009, U.S. Appl. No. 11/278,551, filed Apr. 4, 2006, 64 pgs.
Response dated Nov. 30, 2007, U.S. Appl. No. 11/278,551, filed Apr. 4, 2006, 25 pgs.
Response dated Dec. 19, 2006, U.S. Appl. No. 11/278,551, filed Apr. 4, 2006, 4 pgs.
Examiner's Search Strategy dated Apr. 13, 2009, U.S. Appl. No. 11/278,551, filed Apr. 4, 2006, 2 pgs.
Examiner's Search Strategy dated Jun. 1, 2007, U.S. Appl. No. 11/278,551, filed Apr. 4, 2006, 10 pgs.
Examiner's Search Strategy dated Jun. 26, 2006, U.S. Appl. No. 11/278,551, filed Apr. 4, 2006, 19 pgs.
Examiner's Search Strategy dated Jul. 9, 2008, U.S. Appl. No. 11/278,551, filed Apr. 4, 2006, 6 pgs.
Examiner's Search Strategy dated Dec. 28, 2009, U.S. Appl. No. 11/278,551, filed Apr. 4, 2006, 3 pgs.
Final Office Action dated Sep. 12, 2008, U.S. Appl. No. 11/381,590, filed Apr. 4, 2006, 10 pgs.
Office Action dated Apr. 3, 2007, U.S. Appl. No. 11/381,590, filed Apr. 4, 2006, 8 pgs.
Office Action dated Dec. 27, 2007, U.S. Appl. No. 11/381,590, filed Apr. 4, 2006, 8 pgs.
Response dated Jun. 26, 2008, U.S. Appl. No. 11/381,590, filed Apr. 4, 2006, 7 pgs.
Amendment and Reply dated Oct. 3, 2007, U.S. Appl. No. 11/381,590, filed Apr. 4, 2006, 8 pgs.

Examiner's Search Strategy dated Mar. 30, 2007, U.S. Appl. No. 11/381,590, filed Apr. 4, 2006, 48 pgs.
Office Action dated Mar. 23, 2009, U.S. Appl. No. 11/383,796, filed May 17, 2006; 11 pgs.
Examiner's Search Strategy dated Mar. 23, 2009, U.S. Appl. No. 11/383,796, filed May 17, 2006; 2 pgs.
Office Action dated Mar. 19, 2009, U.S. Appl. No. 11/383,793, filed May 17, 2006, 12 pgs.
Examiner's Search Strategy dated Mar. 19, 2009, U.S. Appl. No. 11/383,793, filed May 17, 2006, 3 pgs.
Advisory Action dated Feb. 10, 2009, U.S. Appl. No. 11/381,130, filed May 2, 2006, 3 pgs.
Final Office Action dated Jul. 18, 2008, U.S. Appl. No. 11/381,130, filed May 2, 2006, 17pgs.
Office Action dated Oct. 9, 2007, U.S. Appl. No. 11/381,130, filed May 2, 2006, 13 pgs.
Response to Final Office Action dated Jan. 21, 2009, U.S. Appl. No. 11/381,130 filed May 2, 2006, 13 pgs.
Response dated Apr. 9, 2008, U.S. Appl. No. 11/381,130, filed May 2, 2006, 36 pgs.
Office Action dated Jun. 1, 2009, U.S. Appl. No. 11/364,306, filed Feb. 28, 2006, 18 pgs.
Examiner's Search Strategy dated Jun. 1, 2009, U.S. Appl. No. 11/364,306, 3 pgs.
Final Office Action dated Sep. 4, 2008, U.S. Appl. No. 11/364,153, filed Feb. 28, 2006, 12 pgs.
Office Action dated Nov. 29, 2007, U.S. Appl. No. 11/364,153, filed Feb. 28, 2006, 11 pgs.
Response dated May 29, 2008, U.S. Appl. No. 11/364,153, filed Feb. 28, 2006, 62 pgs.
Office Action dated Apr. 29, 2009, U.S. Appl. No. 11/364,785, filed Feb. 28, 2006, 23 pgs.
Examiner's Search Strategy dated Apr. 29, 2009, U.S. Appl. No. 11/364,785, filed Feb. 28, 2006, 19 pgs.
Office Action dated Apr. 9, 2009, U.S. Appl. No. 12/170,884, filed Jul. 10, 2008, 10 pgs.
Response dated Oct. 9, 2009, U.S. Appl. No. 12/170,884, filed Jul. 10, 2008, 3 pgs.
Examiner's Search Strategy dated Feb. 19, 2010, U.S. Appl. No. 12/170,884, filed Jul. 10, 2008, 26 pgs.
Examiner's Interview Summary dated Feb. 19, 2010, U.S. Appl. No. 12/170,884, filed Jul. 10, 2008, 4 pgs.
Notice of Allowance dated Feb. 19, 2010, U.S. Appl. No. 12/170,884, filed Jul. 10, 2008, 5 pgs.
Office Action dated Mar. 5, 2009, U.S. Appl. No. 11/740,959, filed Apr. 27, 2007, 30 pgs.
Response dated Sep. 3, 2009, U.S. Appl. No. 11/740,959, filed Apr. 27, 2007, 12 pgs.
Examiner's Search Strategy dated Mar. 5, 2009, U.S. Appl. No. 11/740,959, filed Apr. 27, 2007, 12 pgs.
Final Office Action dated Jan. 20, 2010; U.S. Appl. No. 11/740,959, filed Apr. 27, 2007, 33 pgs.
Examiner's Search Strategy dated Jan. 20, 2010, U.S. Appl. No. 11/740,959, filed Apr. 27, 2007, 6 pgs.
Office Action dated Apr. 13, 2009, U.S. Appl. No. 11/097,939, filed Apr. 4, 2005, 12 pgs.
Amendment and Response dated Sep. 14, 2009, U.S. Appl. No. 11/097,939, filed Apr. 4, 2005, 8 pgs.
Examiner's Search Strategy dated Apr. 13, 2009, U.S. Appl. No. 11/097,939, filed Apr. 4, 2005, 3 pgs.
Final Office Action dated Feb. 17, 2010, U.S. Appl. No. 11/097,939, filed Apr. 4, 2005, 16 pgs.
Examiner's Search Strategy dated Feb. 17, 2010, U.S. Appl. No. 11/097,939, filed Apr. 4, 2005, 2 pgs.
Office Action dated Mar. 19, 2009, U.S. Appl. No. 11/554,855, filed Oct. 31, 2006, 11 pgs.
Response dated Aug. 19, 2009, U.S. Appl. No. 11/554,855, filed Oct. 31, 2006, 7 pgs.
Examiner's Search Strategy dated Mar. 19, 2009, U.S. Appl. No. 11/554,855, filed Oct. 31, 2006, 3 pgs.
Office Action dated Dec. 4, 2009, U.S. Appl. No. 11/554,855, filed Oct. 31, 2006, 15 pgs.
Examiner's Search Strategy dated Dec. 4, 2009, U.S. Appl. No. 11/554,855, filed Oct. 31, 2006, 3 pgs.
Office Action dated Mar. 19, 2009, U.S. Appl. No. 11/745,515, filed May 8, 2007, 11 pgs.
Office Action dated Dec. 4, 2009, U.S. Appl. No. 11/745,515, filed May 8, 2007, 16 pgs.
Examiner's Search Strategy dated Mar. 19, 2009, U.S. Appl. No. 11/745,515, filed May 8, 2007, 3 pgs.
Response dated Aug. 19, 2009, U.S. Appl. No. 11/745,515, filed May 8, 2007, 8 pgs.
Examiner's Search Strategy dated Dec. 4, 2009, U.S. Appl. No. 11/745,515, filed May 8, 2007, 3 pgs.
Office Action dated Oct. 11, 2005, U.S. Appl. No. 10/882,613, filed Jul. 1, 2004, 7 pgs.
Examiner's Search Strategy dated Oct. 2, 2005, U.S. Appl. No. 10/882,613, filed Jul. 1, 2004, 17 pgs.
Advisory Action dated Mar. 16, 2007, U.S. Appl. No. 10/444,892, filed May 22, 2003, 2 pgs.
Advisory Action dated Mar. 29, 2007, U.S. Appl. No. 10/444,892, filed May 22, 2003, 3 pgs.
Examiner's Interview Summ. Dated Oct. 4, 2007, U.S. Appl. No. 10/444,892, filed May 22, 2003, 2 pgs.
Final Office Action dated Aug. 29, 2006, U.S. Appl. No. 10/444,892, filed May 22, 2003, 7 pgs.
Office Action dated Mar. 1, 2006, U.S. Appl. No. 10/444,892, filed May 22, 2003, 5 pgs.
Amendment After Final dated Feb. 28, 2007, U.S. Appl. No. 10/444,892, filed May 22, 2003, 8 pgs.
Amendment dated Jun. 27, 2006, U.S. Appl. No. 10/444,892, filed May 22, 2003, 5 pgs.
Office Action dated Jul. 2, 2007, U.S. Appl. No. 11/110,449, filed Apr. 20, 2005, 11 pgs.
Examiner's Search Strategy dated Jun. 20, 2007, U.S. Appl. No. 11/110,449, filed Apr. 20, 2005, 7 pgs.
Office Action dated Jun. 29, 2009, U.S. Appl. No. 11/960,957, filed Oct. 20, 2007, 12 pgs.
Response dated Dec. 29, 2009, U.S. Appl. No. 11/960,957, filed Oct. 20, 2007, 10 pgs.
Examiner's Search Strategy dated Jun. 29, 2009, U.S. Appl. No. 11/960,957, filed Oct. 20, 2007, 1 pgs.
Notice of Non-Compliant Amendment dated Mar. 10, 2010, U.S. Appl. No. 11/960,957, filed Oct. 20, 2007, 2 pgs.
Amendment and Response to Notice of Non-Compliant Amendment dated Apr. 9, 2010, U.S. Appl. No. 11/960,957, filed Oct. 20, 2007, 5 pgs.
Office Action dated Jan. 26, 2007, U.S. Appl. No. 11/178,716, filed Jul. 11, 2005, 8 pgs.
Office Action dated Apr. 14, 2006, U.S. Appl. No. 11/178,716, filed Jul. 11, 2005, 8 pgs.
Amendment dated Jul. 25, 2006, U.S. Appl. No. 11/178,716, filed Jul. 11, 2005, 5 pgs.
Examiner's Search Strategy dated Jan. 21, 2007, U.S. Appl. No. 11/178,716, filed Jul. 11, 2005, 1 pg.
Examiner's Search Strategy dated Mar. 30, 2006, U.S. Appl. No. 11/178,716, filed Jul. 11, 2005, 15 pgs.
Examiner's Search Strategy dated Apr. 11, 2006, U.S. Appl. No. 11/178,716, filed Jul. 11, 2005, 1 pg.
Final Office Action dated May 18, 2007, U.S. Appl. No. 11/218,107, filed Sep. 1, 2005, 11 pgs.
Office Action dated Aug. 15, 2006, U.S. Appl. No. 11/218,107, filed Sep. 1, 2005, 8 pgs.
Response dated Feb. 14, 2007, U.S. Appl. No. 11/218,107, filed Sep. 1, 2005, 4 pgs.
Examiner's Search Strategy dated Jun. 30, 2006, U.S. Appl. No. 11/218,107, filed Sep. 1, 2005, 8 pgs.
Examiner's Search Strategy dated Aug. 11, 2006, U.S. Appl. No. 11/218,107, filed Sep. 1, 2005, 2 pgs.
Office Action dated Aug. 26, 2008, U.S. Appl. No. 11/940,655, filed Nov. 15, 2007, 7 pgs.
Office Action dated Jan. 25, 2010, U.S. Appl. No. 11/837,957, filed Aug. 13, 2007, 11 pgs.
Examiner's Search Strategy dated Jan. 25, 2010, U.S. Appl. No. 11/837,957, 6 pgs.

Examiner's Interview Summ. dated Oct. 2, 2009, U.S. Appl. No. 11/837,959, filed Aug. 13, 2007, 2 pgs.
Office Action dated Jul. 20, 2009, U.S. Appl. No. 11/837,959, filed Aug. 13, 2007, 8 pgs.
Examiner's Search Strategy dated Jul. 20, 2009, U.S. Appl. No. 11/837,959, filed Aug. 13, 2007, 5 pgs.
Final Office Action dated Mar. 25, 2010, U.S. Appl. No. 11/837,959, filed Aug. 13, 2007, 12 pgs.
Response dated Jan. 20, 2010, U.S. Appl. No. 11/837,959, filed Aug. 13, 2007, 11 pgs.
Ferger et al., Flibanserin, a drug intended for treatment of hypoactive sexual desire disorder in pre-menopausal women, affects spontaneous motor activity and brain neurochemistry in female rates, Naunyn Schmiedebergs Arch Pharmacol., Apr. 27, 2010, pp. 1-17 (epub ahead of print).
Aubert et al., Comparison of Flibanserin With the 5-Ht1a Agonist (+)-8-Oh-Dpat in Affecting Interactions Between Male-Female Marmoset Pairs, J. Sex Med., May 2010, 7(s3):118. (abstract).
Aubert et al., Initial PET Assessment of Flibanserin-induced Neural Changes in Female Marmoset Monkeys, J. Sex Med., May 2010, 7(s3):131. (abstract).
Aubert et al., Chronic Treatment of Female Marmoset Monkeys with (+)-8-OH-DPAT or Flibanserin Differentially Alters Response of the Hypothalamic-Pituitary-Adrenal Axis to Restraint and Acute Serotonergic Challenge, J. Sex Med., May 2010, 7(s3):131. (abstract).
Gelez et al., Chronic Flibanserin Treatment Increases Solicitations in the Female Rat, J. Sex Med., May 2010, 7(s3):118. (abstract).
Allers et al., Acute and Repeated Flibanserin Administration in Female Rats Modulates Monoamines Differentially Across Brain Areas: A Microdialysis Study, J. Sex Med., Feb. 2010, 33 pgs. (Epub ahead of print).
Goldfischer et al., Efficacy of Continued Flibanserin Treatment on Sexual Desire, Satisfying Sexual Events and Sexual Functioning in Premenopausal Women With HSDD: Results From the Researching Outcomes on Sustained Efficacy (ROSE) Study, International Society for the Study of Womens Sexual Health (ISSWSH) annual meeting, 2008, 17 pgs. (oral presentation).
Final Office Action dated May 27, 2010, U.S. Appl. No. 11/278,551, filed Apr. 4, 2006, 8 pgs.
Examiner's Search Strategy dated May 27, 2010, U.S. Appl. No. 11/278,551, filed Apr. 4, 2006, 3 pgs.
Response dated Jun. 4, 2010, U.S. Appl. No. 11/554,855, filed Oct. 31, 2006, 10 pgs.
Response dated Jun. 4, 2010, U.S. Appl. No. 11/745,515, filed May 8, 2007, 8 pgs.
Restriction Requirement dated May 24, 2004 U.S. Appl. No. 10/210,474, filed Aug. 1, 2002 now US Pat. No. 7183410, issued Feb. 27, 2007, 6 pgs.
Response to Restriction Requirement dated Jun. 9, 2004 U.S. Appl. No. 10/210,474, filed Aug. 1, 2002 now US Pat. No. 7183410, issued Feb. 27, 2007, 2 pgs.
Restriction Requirement dated Aug. 20, 2008, U.S. Appl. No. 11/097,939, filed Apr. 4, 2005, 8 pgs.
Response to Restriction Requirement dated Feb. 12, 2009, U.S. Appl. No. 11/097,939, filed Apr. 4, 2005, 2 pgs.
Restriction Requirement dated Feb. 8, 2007, U.S. Appl. No. 11/110,449, filed Apr. 20, 2005, 8 pgs.
Response to Restriction Requirement dated Jun. 7, 2007, U.S. Appl. No. 11/110,449, filed Apr. 20, 2005, 2 pgs.
Restriction Requirement dated Dec. 23, 2008, U.S. Appl. No. 11/187,422, filed Jul. 22, 2005, 11 pgs.
Restriction Requirement dated May 23, 2007, U.S. Appl. No. 11/364,153, filed Feb. 28, 2006, 7 pgs.
Response to Restriction Requirement dated Sep. 24, 2007, U.S. Appl. No. 11/364,153, filed Feb. 28, 2006, 2 pgs.
Restriction Requirement dated Dec. 18, 2006, U.S. Appl. No. 11/381,590, filed Apr. 4, 2006, 7 pgs.
Response to Restriction Requirement dated Mar. 9, 2007, U.S. Appl. No. 11/381,590, filed Apr. 4, 2006, 2 pgs.
Restriction Requirement dated Aug. 18, 2008; U.S. Appl. No. 11/740,959, filed Apr. 27, 2007, 9 pgs.
Response to Restriction Requirement dated Nov. 18, 2008; U.S. Appl. No. 11/740,959, filed Apr. 27, 2007, 6 pgs.
Restriction Requirement dated Aug. 21, 2009, U.S. Appl. No. 11/837,957, filed Aug. 13, 2007, 7 pgs.
Response to Restriction Requirement dated Sep. 21, 2009, U.S. Appl. No. 11/837,957, filed Aug. 13, 2007, 2 pgs.
Restriction Requirement dated Jun. 21, 2010, U.S. Appl. No. 11/956,949, filed Dec. 14, 2007, 7 pgs.
Restriction Requirement dated Feb. 5, 2009, U.S. Appl. No. 11/960,957, filed Oct. 20, 2007, 8 pgs.
Response to Restriction Requirement dated Mar. 4, 2009, U.S. Appl. No. 11/960,957, filed Oct. 20, 2007, 2 pgs.
Restriction Requirement dated May 4, 2010, U.S. Appl. No. 12/279,589, filed Sep. 26, 2008, 9 pgs.
RCE dated May 19, 2010, U.S. Appl. No. 12/170,884, filed Jul. 10, 2008, 3 pgs.
Examiner's Interview dated Apr. 15, 2009, U.S. Appl. No. 11/524,268, filed Sep. 21, 2006, 4pgs.
Examiner's Interview dated Oct. 23, 2007, U.S. Appl. No. 11/524,268, filed Sep. 21, 2006, 1 pg.
Notice of Allowance dated Jan. 11, 2010, U.S. Appl. No. 11/524,268, filed Sep. 21, 2006, 7 pgs.
Office Action dated Feb. 11, 2008, U.S. Appl. No. 11/524,268, filed Sep. 21, 2006, 15 pgs.
Office Action dated May 2, 2007, U.S. Appl. No. 11/524,268, filed Sep. 21, 2006, 10 pgs.
Office Action dated Dec. 1, 2008, U.S. Appl. No. 11/524,268, filed Sep. 21, 2006, 16 pgs.
Amendment dated Jun. 1, 2009, U.S. Appl. No. 11/524,268, filed Sep. 21, 2006, 64 pgs.
Response dated Aug. 11, 2008, U.S. Appl. No. 11/524,268, filed Sep. 21, 2006, 15 pgs.
Response dated Nov. 2, 2007, U.S. Appl. No. 11/524,268, filed Sep. 21, 2006, 32 pgs.
Examiner's Search Strategy dated Jan. 11, 2010, U.S. Appl. No. 11/524,268, filed Sep. 21, 2006, 5 pgs.
Examiner's Search Strategy dated Dec. 1, 2008, U.S. Appl. No. 11/524,268, filed Sep. 21, 2006, 4 pgs.
RCE dated Apr. 9, 2010, U.S. Appl. No. 11/524,268, filed Sep. 21, 2006, 2 pgs.
Office Action dated Jan. 11, 2010, U.S. Appl. No. 11/837,962, filed Aug. 13, 2007, 17 pgs.
Examiner's Search Strategy dated Jan. 11, 2010, U.S. Appl. No. 11/837,962, filed Aug. 13, 2007, 8 pgs.
Response dated Jun. 11, 2010 U.S. Appl. No. 11/837,962, filed Aug. 13, 2007, 16 pgs.
Restriction Requirement dated Sep. 9, 2009, U.S. Appl. No. 11/837,962, filed Aug. 13, 2007, 10 pgs.
Response to Restriction Requirement dated Sep. 25, 2009, U.S. Appl. No. 11/837,962, filed Aug. 13, 2007, 2 pgs.
Office Action dated Jan. 14, 2010, U.S. Appl. No. 12/091,848, filed Apr. 28, 2008, 5 pgs.
Examiner's Search Strategy dated Jan. 14, 2010, U.S. Appl. No. 12/091,848, filed Apr. 28, 2008, 47 pgs.
Response dated Jun. 14, 2010 U.S. Appl. No. 12/091,848, filed Apr. 28, 2008, 5 pgs.
Restriction Requirement dated Oct. 7, 2009, U.S. Appl. No. 12/091,848, filed Apr. 28, 2008, 5 pgs.
Response to Restriction Requirement dated Nov. 9, 2009, U.S. Appl. No. 12/091,848, filed Apr. 28, 2008, 9 pgs.
Notice of Non-Compliant Amendment dated Jun. 22, 2010 U.S. Appl. No. 12/091,848, filed Apr. 28, 2008, 2 pgs.
Response to Notice of Non-Compliant Amdmt dated Jun. 23, 2010 U.S. Appl. No. 12/091,848, filed Apr. 28, 2008, 6 pgs.
Final Office Action dated Jul. 9, 2010; U.S. Appl. No. 11/960,957, filed Dec. 20, 2007, 9 pgs.
Response to Final Office Action dated Jul. 20, 2010; U.S. Appl. No. 11/740,959, filed Apr. 27, 2007, 14 pgs.
Response to Office Action dated Jul. 26, 2010; U.S. Appl. No. 11/837,957, filed Aug. 13, 2007, 11 pgs.
Restriction Requirement dated Oct. 4, 2005; U.S. Appl. No. 10/444,892, filed May 22, 2003, 7 pgs.

Response to Restriction Requirement dated Dec. 1, 2005; U.S. Appl. No. 10/444,892, filed May 22, 2003, 2 pgs.
RCE dated Jul. 20, 2010; U.S. Appl. No. 11/740,959, filed Apr. 27, 2007, 3pgs.
FDA (U.S. Food and Drug Administration); Reproductive Health Drugs Advisory Committee Meeting Announcement; URL: http://www.fda.gov/AdvisoryCommittees/Calendar/ucm210886.htm; Jun. 18, 2010; 1 pg.
Background Document for Meeting of Advisory Committee for Reproductive Health Drugs (Jun. 8, 2010); NDA 22-526 Flibanserin; Boehringer Ingelheim; May 20, 2010; 80 pgs.
Anonymous, Gel significantly increases sexual-activity in surgically menopausal women, Online, Nov. 1, 2004, XP002455243, Retrieved from the Internet: URL:http/www.news-medical.net/print_article.asp?id=5960>[retrieved on Oct. 17, 2007] 8 pgs.
Eriksson, Serotonin reuptake inhibitors for the treatment of premenstrual dysphoria, Intl. Clin. Psychopharm, 1999, 14Supp2:S27-S33.
Steiner et al., Serotonin re-uptake inhibitors in the treatment of premenstrual dysphoria: Current status of knowledge, 1997, 1:241-247.
Office Action dated Oct. 26, 2010, U.S. Appl. No. 11/278,551, filed Apr. 4, 2006, 10 pgs.
Office Action dated Oct. 5, 2010; U.S. Appl. No. 11/956,949, filed Dec. 14, 2007, 10 pgs.
Advisory Action dated Nov. 8, 2010; U.S. Appl. No. 11/960,957, filed Dec. 20, 2007, 3 pgs.
Acknowledgment of Priority Document dated Nov. 4, 2010; U.S. Appl. No. 12/091,848, filed Apr. 28, 2008, 1 pg.
Notice of Allowance dated Nov. 15, 2010; U.S. Appl. No. 12/091,848, filed Apr. 28, 2008, 4 pgs.
RCE dated Dec. 20, 2010; U.S. Appl. No. 12/091,848, filed Apr. 28, 2008, 3 pgs.
Office Action dated Dec. 30, 2010; U.S. Appl. No. 12/390,665, filed Feb. 23, 2009, 9 pgs.
U.S. Appl. No. 12/987,388, filed Jan. 10, 2011, Mendla et al.
Response to Final Office Action dated Jan. 20, 2011; U.S. Appl. No. 11/745,515, filed May 8, 2007, 7 pgs.
Response to Final Office Action dated Jan. 20, 2011; U.S. Appl. No. 11/554,855, filed Oct. 31, 2006, 9 pgs.
Response to Office Action dated Jan. 28, 2011, U.S. Appl. No. 11/278,551, filed Apr. 4, 2006, 7 pgs.
Response to Final Office Action dated Feb. 7, 2011; U.S. Appl. No. 11/837,957, filed Aug. 13, 2007, 9 pgs.
RCE dated Feb. 15, 2011; U.S. Appl. No. 11/837,962, filed Aug. 13, 2007, 2 pgs.
Response to Final Office Action dated Feb. 15, 2011; U.S. Appl. No. 11/837,962, filed Aug. 13, 2007, 15 pgs.
Notice of Allowance dated Feb. 16, 2011; U.S. Appl. No. 12/091,848, filed Apr. 28, 2008, 8 pgs.
Advisory Action dated Feb. 17, 2011; U.S. Appl. No. 11/837,957, filed Aug. 13, 2007, 3 pgs.
Notice of Appeal dated Feb. 22, 2011; U.S. Appl. No. 11/745,515, filed May 8, 2007, 1 pgs.
Notice of Appeal dated Feb. 22, 2011; U.S. Appl. No. 11/554,855, filed Oct. 31, 2006, 1 pgs.
Advisory Action dated Mar. 2, 2011; U.S. Appl. No. 11/745,515, filed May 8, 2007, 3 pgs.
Advisory Action dated Mar. 2, 2011; U.S. Appl. No. 11/554,855, filed Oct. 31, 2006, 3 pgs.
RCE dated Mar. 7, 2011; U.S. Appl. No. 11/837,957, filed Aug. 13, 2007, 2 pgs.
Response to Final Office Action dated Mar. 7, 2011; U.S. Appl. No. 11/837,957, filed Aug. 13, 2007, 9 pgs.
Response to Office Action dated Mar. 14, 2011; U.S. Appl. No. 11/097,939, filed Apr. 4, 2005, 20 pgs.
Interview Summary dated Mar. 15, 2011; U.S. Appl. No. 11/097,939, filed Apr. 4, 2005, 4 pgs.

* cited by examiner

USE OF FLIBANSERIN IN THE TREATMENT OF OBESITY

RELATED APPLICATIONS

This application is filed pursuant to 35 U.S.C. 371 and constitutes the national stage of International Application PCT/EP2006/064825 filed Jul. 31, 2006.

The invention relates to a method for the treatment of obesity and related diseases, comprising the administration of a therapeutically effective amount of Flibanserin. The invention relates further to new pharmaceutical compositions for the treatment of obesity and related diseases.

BACKGROUND OF THE INVENTION

The intake of food and its conversion in the body is an essential part of life for all living creatures. Therefore, deviations in the intake and conversion of food generally lead to problems and also illness. The changes in the lifestyle and nutrition of humans, particularly in industrialised countries, have promoted morbid overweight (also known as corpulence or obesity) in recent decades.

The prevalence of obesity has risen significantly in the past decade in the United States and many other developed countries, (Fiegal et al, Int. J. Obesity 22:39-47 (1998), Mokdad et al, JAMA 282:1519-1522 (1999)). Because obesity is associated with a significantly elevated risk for diabetes, especially for type 2 diabetes, dyslipidaemia, arteriosclerosis, coronary heart disease, hypertension, and numerous other major illnesses, and overall mortality from all causes (Must et al, JAMA 282:1523-1529 (1999), Calle et al, N. Engl. J. Med. 341:1097-1105 (1999)), weight reduction is critical for the obese patient (Blackburn, Am. J. Clin. Nujtr. 69:347-349 (1999), Galuska et al, JAMA 282:1576 (1999)). Moreover, high body weight alone puts an increased strain on the support and mobility apparatus, which can lead to chronic pain and diseases such as arthritis or osteoarthritis. Thus, obesity is a serious health problem for society.

There is good evidence that pharmacotherapy can enhance weight loss when combined with interventions aimed at changing life style (National Heart, Lung and Blood Institute, Clinical guidelines on the identification, evaluation, and treatment of overweight and obesity in adults: the evidence report, NIH Publication No. 98-4083, September 1998). Yet, the available pharmacological therapies to facilitate weight loss fail to provide adequate benefit to many obese patients because of side effects, contraindications or lack of positive response (National Heart, Lung and Blood Institute, Clinical guidelines on the identification, evaluation, and treatment of overweight and obesity in adults: the evidence report, NIH Publication No. 98-4083, September 1998). Hence, there is impetus for developing new and alternative treatments for management of obesity.

Apart from physical activity and a change in nutrition, there is currently no convincing treatment option for effectively reducing body weight. However, as obesity is a major risk factor in the development of serious and even life-threatening diseases, it is all the more important to have access to pharmaceutical active substances for the prevention and/or treatment of obesity.

DESCRIPTION OF THE INVENTION

The compound 1-[2-(4-(3-trifluoromethyl-phenyl)piperazin-1-yl)ethyl]-2,3-dihydro-1H-benzimidazol-2-one (Flibanserin) is disclosed in form of its hydrochloride in European Patent Application EP-A-526434 and has the following chemical structure:

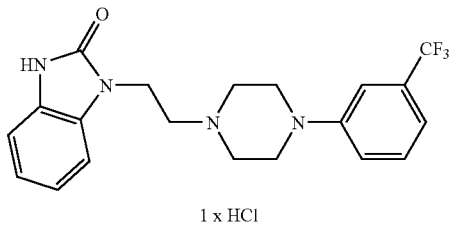

Flibanserin shows affinity for the 5-$HT_{1A}$ receptor and the 5-$HT_2$-receptor family. It is therefore a promising therapeutic agent for the treatment of a variety of diseases, for instance depression, schizophrenia and anxiety.

Surprisingly it has been found that Flibanserin, optionally in form of the free base, the pharmacologically acceptable acid addition salts and/or optionally in form of the hydrates and/or solvates thereof proved to be a weight-loss agent and therefore is useful to treat obesity and related diseases.

As used herein, the term "obesity" means an excess of adipose tissue in the body. In this connection, obesity is fundamentally to be seen as the increased level of fatness which leads to a health risk. There is no sharp distinction between normal individuals, overweight individuals and those suffering from obesity, but the health risk accompanying obesity is presumed to rise continuously as the level of fatness increases. For simplicity's sake, in the present invention, individuals with a Body Mass Index (BMI), which is defined as the body weight measured in kilograms divided by the height (in meters) squared, above a value of 25 and more particularly above 30, are preferably regarded as suffering from obesity.

One object of the present invention is directed to the use of Flibanserin, optionally in form of the free base, the pharmacologically acceptable acid addition salts and/or optionally in form of the hydrates and/or solvates thereof, for the preparation of a medicament for the treatment and/or prevention of obesity.

The indication obesity includes in particular exogenic obesity, hyperinsulinaemic obesity, hyperplasmic obesity, hyperphyseal adiposity, hypoplasmic obesity, hypothyroid obesity, hypothalamic obesity, symptomatic obesity, infantile obesity, upper body obesity, alimentary obesity, hypogonadal obesity and central obesity.

Therefore, the present invention is directed also to the use of Flibanserin, optionally in form of the free base, the pharmacologically acceptable acid addition salts and/or optionally in form of the hydrates and/or solvates thereof, for the preparation of a medicament for the treatment and/or prevention of exogenic obesity, hyperinsulinaemic obesity, hyperplasmic obesity, hyperphyseal adiposity, hypoplasmic obesity, hypothyroid obesity, hypothalamic obesity, symptomatic obesity, infantile obesity, upper body obesity, alimentary obesity, hypogonadal obesity and central obesity.

In another embodiment, this invention relates to the use of Flibanserin, optionally in form of the free base, the pharmacologically acceptable acid addition salts and/or optionally in form of the hydrates and/or solvates thereof, for the preparation of a medicament for promoting, increasing or facilitating weight loss.

Furthermore, this invention relates to the use of Flibanserin, optionally in form of the free base, the pharmacologically acceptable acid addition salts and/or optionally in form of the hydrates and/or solvates thereof, for the preparation of a medicament for prevention of body weight gain.

In another embodiment, this invention relates to the use of Flibanserin, optionally in form of the free base, the pharmacologically acceptable acid addition salts and/or optionally in form of the hydrates and/or solvates thereof, for the preparation of a medicament for inhibiting or reducing appetite.

In another embodiment, this invention relates to the use of Flibanserin, optionally in form of the free base, the pharmacologically acceptable acid addition salts and/or optionally in form of the hydrates and/or solvates thereof, for the preparation of a medicament for the treatment and/or prevention of diseases and/or disorders associated with obesity, such as the metabolic syndrome (syndromeX), hypertension, osteoarthritis, diabetes, especially type II diabetes, complications of diabetes including diabetic retinopathy, diabetic neuropathy, diabetic nephropathy, insulin resistance, pathological glucose tolerance, encephalorrhagia, heart diseases, cardiac insufficiency, arteriosclerosis, arthritis, gonitis, stroke and dyslipidaemia, preferably metabolic syndrome, diabetes and dyslipidaemia, comprising the administration of a therapeutically effective amount of Flibanserin, optionally in form of the free base, the pharmacologically acceptable acid addition salts and/or optionally in form of the hydrates and/or solvates thereof.

Another embodiment of the present invention relates to a method of treating and/or preventing the above mentioned diseases and/or disorders comprising the administration of a therapeutically effective amount of Flibanserin, optionally in form of the free base, the pharmacologically acceptable acid addition salts and/or optionally in form of the hydrates and/or solvates thereof.

For the treatment of the aforementioned diseases, Flibanserin, optionally in form of the free base, the pharmacologically acceptable acid addition salts and/or optionally in form of the hydrates and/or solvates thereof may also be co-administered with a second active substance selected from the group consisting of active substances for the treatment of diabetes,
active substances for the treatment of diabetic complications,
active substances for the treatment of obesity,
active substances for the treatment of high blood pressure,
active substances for the treatment of hyperlipidaemia, including arteriosclerosis,
active substances for the treatment of dyslipidaemia, including arteriosclerosis,
active substances for the treatment of arthritis.

Examples of active substances for the treatment of diabetes are insulin sensitisers, insulin secretion accelerators, biguanides, insulins, α-glucosidase inhibitors, β3 adrenoreceptor agonists.

Insulin sensitisers include glitazones, particularly pioglitazone and its salts (preferably hydrochloride), troglitazone, rosiglitazone and its salts (preferably maleate), JTT-501, GI-262570, MCC-555, YM-440, DRF-2593, BM-13-1258, KRP-297, R-119702 and GW-1929.

Insulin secretion accelerators include sulphonylureas, such as for example tolbutamide, chloropropamide, tolazamide, acetohexamide, glyclopyramide and its ammonium salts, glibenclamide, gliclazide, glimepiride. Further examples of insulin secretion accelerators are repaglinide, nateglinide, mitiglinide (KAD-1229) and JTT-608.

Biguanides include metformin, buformin and phenformin.

Insulins include those obtained from animals, particularly cattle or pigs, semisynthetic human insulins which are synthesised enzymatically from insulin obtained from animals, human insulin obtained by genetic engineering, e.g. from *Escherichi coli* or yeasts. Moreover, the term insulin also includes insulin-zinc (containing 0.45 to 0.9 percent by weight of zinc) and protamine-insulin-zinc obtainable from zinc chloride, protamine sulphate and insulin. Insulin may also be obtained from insulin fragments or derivatives (for example INS-1, etc.).

Insulin may also include different kinds, e.g. with regard to the onset time and duration of effect ("ultra immediate action type", "immediate action type", "two phase type", "intermediate type", "prolonged action type", etc.), which are selected depending on the pathological condition of the patient.

α-Glucosidase inhibitors include acarbose, voglibose, miglitol, emiglitate.

$\beta_3$ Adreno receptor agonists include AJ-9677, BMS-196085, SB-226552, AZ40140.

Active substances for the treatment of diabetes other than those mentioned above include ergoset, pramlintide, leptin, BAY-27-9955 as well as glycogen phosphorylase inhibitors, sorbitol dehydrogenase inhibitors, protein tyrosine phosphatase 1B inhibitors, dipeptidyl protease inhibitors, glipazide, glyburide.

Active substances for the treatment of diabetic complications include for example aldose reductase inhibitors, glycation inhibitors and protein kinase C inhibitors, DPPIV blockers, GLP-1 or GLP-2 analogues and SGLT-2 inhibitors.

Aldose reductase inhibitors are for example tolrestat, epalrestat, imirestat, zenarestat, SNK-860, zopolrestat, ARI-50i, AS-3201.

An example of a glycation inhibitor is pimagedine.

Protein Kinase C inhibitors are for example NGF, LY-333531.

DPPIV blockers are for example LAF237 (Novartis), MK431 (Merck) as well as 815541, 823093 and 825964 (all GlaxoSmithkline).

GLP-1 analogues are for example Liraglutide (NN2211) (NovoNordisk), CJC1131 (Conjuchem), Exenatide (Amylin).

SGLT-2 inhibitors are for example AVE-2268 (Aventis) and T-1095 (Tanabe, Johnson&Johnson).

Active substances other than those mentioned above for the treatment of diabetic complications include alprostadil, thiapride hydrochloride, cilostazol, mexiletine hydrochloride, ethyl eicosapentate, memantine, pimagedine (ALT-711).

Active substances for the treatment of obesity, other than Flibanserin, include lipase inhibitors and anorectics.

A preferred example of a lipase inhibitor is orlistat.

Examples of preferred anorectics are phenetermine, mazindol, fluoxetine, sibutramine, baiamine, (S)-sibutramine, SR-141716, NGD-95-1.

Active substances other than those mentioned above for the treatment of obesity include lipstatin, Rimonabant and topiramate Moreover for the purposes of this application the active substance group of anti-obesity active substances also includes the anorectics, of which the $\beta_3$ agonists, thyromimetic active substances and NPY antagonists should be emphasised. The range of substances which may be considered as preferred anti-obesity or anorectic active substances is indicated by the following additional list, by way of example: phenylpropanolamine, ephedrine, pseudoephedrine, phenetermine, a cholecystokinin-A (hereinafter referred to as CCK-A) agonist, a monoamine reuptake inhibitor (such as for example sibutramine), a sympathomimetic active substance, a serotonergic active substance (such as for example dexfenfluramine, fenfluramine, a 5-HT2C agonist such as BVT.933 or APD356), a dopamine antagonist (such as for example bromocriptine or pramipexol), a melanocyte-stimulating hormone receptor agonist or mimetic, an analogue of melanocyte-stimulating hormone, a cannabinoid receptor antagonist (Rimonabant, ACOMPLIA™), an MCH antagonist, the OB protein (hereinafter referred to as leptin), a leptin analogue, a fatty acid synthase (FAS) antagonist, a leptin receptor agonist, a galanine antagonist, a GI lipase inhibitor or reducer (such as for example orlistat). Other anorectics include bombesin agonists, dehydroepiandrosterone or its analogues, glucocorticoid receptor agonists and antagonists, orexin receptor antagonists, urocortin binding protein antagonists, agonists of the Glucagon-like Peptide-1 receptor, such as for example exendin, AC 2993, CJC-1131, ZP10 or GRT0203Y, DPPIV inhibitors and ciliary neurotrophic factors, such as for example axokines. In this context mention should also be made of the forms of therapy which produce weight loss by increasing the fatty acid oxidation in the peripheral tissue, such as for example inhibitors of acetyl-CoA carboxylase.

Active substances for the treatment of high blood pressure include inhibitors of angiotensin converting enzyme, calcium antagonists, potassium channel openers and angiotensin II antagonists.

Inhibitors of angiotensin converting enzyme include captopril, enalapril, alacepril, delapril (hydrochloride), lisinopril, imidapril, benazepril, cilazapril, temocapril, trandolapril, manidipine (hydrochloride).

Examples of calcium antagonists are nifedipine, amlodipine, efonidipine, nicardipine.

Potassium channel openers include levcromakalim, L-27152, AL0671, NIP-121.

Angiotensin II antagonists include telmisartan, losartan, candesartan cilexetil, valsartan, irbesartan, CS-866, E4177.

Active substances for the treatment of hyperlipidaemia, including arteriosclerosis, include HMG-CoA reductase inhibitors, fibrate compounds.

HMG-CoA reductase inhibitors include pravastatin, simvastatin, lovastatin, atorvastatin, fluvastatin, lipantil, cerivastatin, itavastatin, ZD-4522 and their salts.

Fibrate compounds include bezafibrate, clinofibrate, clofibrate and simfibrate.

Active substances for the treatment of dyslipidaemia, including arteriosclerosis, include e.g. medicaments which raise the HDL level, such as e.g. nicotinic acid and derivatives and preparations thereof, such as e.g. niaspan, as well as agonists of the nicotinic acid receptor.

Active substances for the treatment of arthritis include NSAIDs (non-steroidal antiinflammatory drugs), particularly COX2 inhibitors, such as for example meloxicam or ibuprofen.

Accordingly, the invention also relates to combining separate pharmaceutical compositions in kit form which may be co-administered separately. Therefore, in a further embodiment the present invention provides a kit comprising a) a first pharmaceutical composition comprising an active substance being not flibanserin, selected from the group consisting of active substances for the treatment of diabetes, active substances for the treatment of diabetic complications, active substances for the treatment of obesity, active substances for the treatment of high blood pressure, active substances for the treatment of hyperlipidaemia, including arteriosclerosis active substances for the treatment of dyslipidaemia, including arteriosclerosis, active substances for the treatment of arthritis, b) a second pharmaceutical composition comprising Flibanserin, optionally in form of the free base, the pharmacologically acceptable acid addition salts and/or optionally in form of the hydrates and/or solvates thereof for the treatment of the above mentioned diseases; and a container for both compositions.

In a preferred embodiment the present invention provides a kit comprising a) a first pharmaceutical composition comprising one or more, preferably one active substance for the treatment of obesity, preferrably orlistat, phenetermine, sibutramine or topiramate; b) a second pharmaceutical composition comprising Flibanserin, optionally in form of the free base, the pharmacologically acceptable acid addition salts and/or optionally in form of the hydrates and/or solvates thereof for the treatment of the above mentioned diseases; and a container for both compositions The term "co-administration", within the present invention means that both active ingredients mentioned above can be taken from the kit and combined for administration together as a composition or as part of the same, unitary dosage form, such as an parenterally or orally administered solution. "Co-administration" also includes administering the components separately (e.g. as tablets or capsules), but as part of the same therapeutic treatment program or regimen. Both components need not be administered at essentially the same time, although they can be if so desired. Thus "co-administration" includes, for example administering all active ingredients as separate dosages or dosage forms and at essentially the same time. The term also includes separate administration at different times, in any order, and if preferred by different routes of administration. An example of a kit is the so-called blister pack well known in the packaging industry particularly for packaging pharmaceutical dosage forms.

Instead of a kit, Flibanserin and the second active substance according to the invention can be combined in one dosage form. Therefore, the present invention also relates to compositions comprising Flibanserin optionally in form of the free base, the pharmacologically acceptable acid addition salts and/or optionally in form of the hydrates and/or solvates thereof and a second active substance active being not flibanserin, selected from the group consisting of active substances for the treatment of diabetes, active substances for the treatment of diabetic complications, active substances for the treatment of obesity, active substances for the treatment of high blood pressure, active substances for the treatment of hyperlipidaemia, including arteriosclerosis active substances for the treatment of dyslipidaemia, including arteriosclerosis, active substances for the treatment of arthritis in one dosage form.

Preferably, the present invention also relates to compositions comprising a) one or more, preferably one active substance for the treatment of obesity preferrably orlistat, phenetermine, sibutramine or topiramate and b) Flibanserin, optionally in form of the free base, the pharmacologically acceptable acid addition salts and/or optionally in form of the hydrates and/or solvates thereof.

Above mentioned kits and compositions can be used for the treatment and/or prevention of obesity like exogenic obesity, hyperinsulinaemic obesity, hyperplasmic obesity, hyperphyseal adiposity, hypoplasmic obesity, hypothyroid obesity, hypothalamic obesity, symptomatic obesity, infantile obesity, upper body obesity, alimentary obesity, hypogonadal obesity and central obesity as well as for promoting, increasing or facilitating of weight loss, for the prevention of body weight gain, and for inhibiting or reducing appetite.

Furthermore the above mentioned kits and compositions can be used for the treatment and/or prevention of diseases and/or disorders associated with obesity, such as the metabolic syndrome (syndromeX), hypertension, osteoarthritis, diabetes, especially type II diabetes, complications of diabetes including diabetic retinopathy, diabetic neuropathy, diabetic nephropathy, insulin resistance, pathological glucose tolerance, encephalorrhagia, heart diseases, cardiac insufficiency, arteriosclerosis, arthritis, gonitis, stroke and dyslipidaemia, preferably metabolic syndrome, diabetes and dyslipidaemia.

As already mentioned above, Flibanserin may be used in form of the free base, optionally in form of its pharmaceutically acceptable acid addition salts and/or optionally in form of the hydrates and/or solvates thereof. Suitable acid addition salts include for example those of the acids selected from, succinic acid, hydrobromic acid, acetic acid, fumaric acid, maleic acid, methanesulphonic acid, lactic acid, phosphoric acid, hydrochloric acid, sulphuric acid, tartaric acid and citric acid. Mixtures of the abovementioned acid addition salts may also be used. From the aforementioned acid addition salts the hydrochloride and the hydrobromide, particularly the hydrochloride, are preferred. If Flibanserin is used in form of the free base, it is preferably used in form of Flibanserin polymorph A as disclosed in WO 03/014079.

The active substances which are suitable to be combined with Flibanserin within the teaching of the instant invention and which are mentioned hereinbefore may also be capable of forming acid addition salts with pharmaceutically acceptable acids. Representative salts include the following: Acetate, Benzenesulfonate, Benzoate, Bicarbonate, Bisulfate, Bitartrate, Borate, Bromide, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isothionate, Lactate, Lactobionate, Laurate, Malate, Maleate, Mandelate, Mesylate, Methylbromide, Methylnitrate, Methylsulfate, Mucate, Napsylate, Nitrate, N-methylglucamine ammonium salt, Oleate, Oxalate, Pamoate (Embonate), Palmitate, Pantothenate, Phosphate/diphosphate, Polygalacturonate, Salicylate, Stearate, Sulfate, Subacetate, Succinate, Tannate, Tartrate, Teoclate, Tosylate, Triethiodide and Valerate.

Furthermore, where the other anti-obesity compounds carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

The active substances which are suitable to be combined with Flibanserin may have chiral centers and occur as racemates, racemic mixtures and as individual diastereomers, or enantiomers with all isomeric forms being included in the present invention. Therefore, where a compound is chiral, the separate enantiomers, substantially free of the other, are included within the scope of the invention. Further included are all mixtures of the two enantiomers. Also included within the scope of the invention are polymorphs and hydrates of the compounds of the instant invention.

The present invention includes within its scope prodrugs of Flibanserin and of the active substances which are suitable to be combined with Flibanserin. In general, such prodrugs will be functional derivatives of the compounds of this invention which are readily convertible in vivo into the required compound.

Flibanserin, optionally used in form of its pharmaceutically acceptable acid addition salts and/or optionally in form of the hydrates and/or solvates thereof, or in form of Flibanserin polymorph A, as well as the other anti-obesity compounds may be incorporated into the conventional pharmaceutical preparation in solid, liquid or spray form. The compositions may, for example, be presented in a form suitable for oral, rectal, parenteral administration or for nasal inhalation: preferred forms includes for example, capsules, tablets, coated tablets, ampoules, suppositories and nasal spray.

The active ingredients may be incorporated in excipients or carriers conventionally used in pharmaceutical compositions such as, for example, talc, arabic gum, lactose, gelatine, magnesium stearate, corn starch, acqueous or non acqueous vehicles, polyvynil pyrrolidone, semisynthetic glicerides of fatty acids, benzalconium chloride, sodium phosphate, EDTA, polysorbate 80. The compositions are advantageously formulated in dosage units, each dosage unit being adapted to supply a single dose of the active ingredient.

Within the instant invention flibanserin is preferably administered in such an amount that per single dosage between 0.01 to 400 mg of flibanserin are applied. Preferred are ranges of between 1.0 to 300 mg, particular preferred 2.0 to 200 mg of flibanserin. Suitable dosage forms may contain for instance 5, 10, 20, 25, 30, 35, 40, 45, 50, 55, 60, 65, 70, 75, 80, 85, 90, 95 or 100 mg of flibanserin. The doses range applicable per day is between 0.1 to 400, preferably between 1.0 to 300, more preferably between 2 to 200 mg. The aforementioned values are based on flibanserin in form of the free base. If flibanserin is applied in form of one of its acid addition salts, the corresponding values are readily calculable from the aforementioned values. Advantageously, flibanserin may be administered in a single daily dose, or the total daily dosage may be administered in divided doses of two, three or four times daily.

The dosage of the active ingredients suitable for coadministration with flibanserin in the compositions of this invention may be varied. However, it is necessary that the amount of the active ingredients be such that a suitable dosage form is obtained. The selected dosage and the dosage form depend upon the desired therapeutic effect, on the route of administration and on the duration of the treatment. Dosage ranges in the combination are approximately one tenth to one times the clinically effective ranges required to induce the desired therapeutic effect, respectively when the compounds are used singly.

In case of the preferred compound orlistat particularly preferred doses per day are in the range of about 100 to 400 mg. In case of the preferred compound sibutramine particularly preferred doses per day are in the range of about 5 to 15 mg. In case of the preferred compound phenetermine particularly preferred doses per day are in the range of about 30 to 90 mg. Suitable dosage forms may contain for instance 5, 10, 15, 20, 25, 30, 35, 40, 45, 50, 55, 60, 65, 70, 75, 80, 85, 90, 95 or 100 mg of the above mentioned compounds. Advantageously, the compounds of the present invention may be administered in a single daily dose, or the total daily dosage may be administered in divided doses of two, three or four times daily.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. of a flavouring such as vanilline or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection are prepared in the usual way, e.g. of with the addition of preservatives such as p-hydroxybenzoates, or stabilisers such as alkali metal salts of ethylenediamine tetraacetic acid, and transferred into injection vials or ampoules.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

The Examples which follow illustrate the present invention without restricting its scope:
Examples of Pharmaceutical Formulations

| A) Tablets | per tablet |
|---|---|
| Flibanserin hydrochloride | 100 mg |
| lactose | 240 mg |
| corn starch | 340 mg |
| polyvinylpyrrolidone | 45 mg |
| magnesium stearate | 15 mg |
| | 740 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| Flibanserin hydrochloride | 80 mg |
| corn starch | 190 mg |
| lactose | 55 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

| C) Coated tablets | per coated tablet |
|---|---|
| Flibanserin hydrochloride | 5 mg |
| corn starch | 41.5 mg |
| lactose | 30 mg |
| polyvinylpyrrolidone | 3 mg |
| magnesium stearate | 0.5 mg |
| | 80 mg |

The active substance, corn starch, lactose and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

| D) Capsules | per capsule |
|---|---|
| Flibanserin hydrochloride | 150 mg |
| Corn starch | 268.5 mg |
| Magnesium stearate | 1.5 mg |
| | 420 mg |

The substance and corn starch are mixed and moistened with water. The moist mass is screened and dried. The dry granules are screened and mixed with magnesium stearate. The finished mixture is packed into size 1 hard gelatine capsules.

| E) Ampoule solution | |
|---|---|
| Flibanserin hydrochloride | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion.

| F) Suppositories | |
|---|---|
| Flibanserin hydrochloride | 50 mg |
| solid fat | 1650 mg |
| | 1700 mg |

The hard fat is melted. At 40° C. the ground active substance is homogeneously dispersed. It is cooled to 38° C. and poured into slightly chilled suppository moulds.

In a particular preferred embodiment of the instant invention, Flibanserin is administered in form of specific film coated tablets. Examples of these preferred formulations are listed below. The film coated tablets listed below can be manufactured according to procedures known in the art (see hereto WO 03/097058).

G) Film coated tablet

| Constituents | mg/tablet |
|---|---|
| Core | |
| Flibanserin | 25.000 |
| Lactose monohydrate | 71.720 |
| Microcrystalline cellulose | 23.905 |
| HPMC (Methocel E5) | 1.250 |
| Carboxymethylcellulose sodium | 2.500 |
| Magnesium stearate | 0.625 |
| Coating | |
| HPMC (Methocel E5) | 1.440 |
| Polyethylene Glycol 6000 | 0.420 |
| Titanium dioxide | 0.600 |
| Talc | 0.514 |
| Iron oxide red | 0.026 |
| Total Film coated tablet | 128.000 |

H) Film coated tablet

| Constituents | mg/tablet |
|---|---|
| Core | |
| Flibanserin | 50.000 |
| Lactose monohydrate | 143.440 |
| Microcrystalline cellulose | 47.810 |
| HPMC (e.g. Pharmacoat 606) | 2.500 |
| Carboxymethylcellulose sodium | 5.000 |
| Magnesium stearate | 1.250 |
| Coating | |
| HPMC (e.g. Pharmacoat 606) | 2.400 |
| Polyethylene Glycol 6000 | 0.700 |
| Titanium dioxide | 1.000 |
| Talc | 0.857 |
| Iron oxide red | 0.043 |
| Total Film coated tablet | 255.000 |

I) Film coated tablet

| Constituents | mg/tablet |
|---|---|
| Core | |
| Flibanserin | 100.000 |
| Lactose monohydrate | 171.080 |
| Microcrystalline cellulose | 57.020 |
| HPMC (e.g. Methocel E5) | 3.400 |
| Carboxymethylcellulose sodium | 6.800 |
| Magnesium stearate | 1.700 |
| Coating | |
| HPMC (e.g. Methocel E5) | 3.360 |
| Polyethylene Glycol 6000 | 0.980 |
| Titanium dioxide | 1.400 |
| Talc | 1.200 |
| Iron oxide red | 0.060 |
| Total Film coated tablet | 347.000 |

J) Film coated tablet

| Constituents | mg/tablet |
|---|---|
| Core | |
| Flibanserin | 2.000 |
| Dibasic Calciumphosphate, anhydrous | 61.010 |
| Microcrystalline cellulose | 61.010 |
| HPMC (Methocel E5) | 1.950 |
| Carboxymethylcellulose sodium | 2.600 |
| Colloidal silicon dioxide | 0.650 |
| Magnesium stearate | 0.780 |
| Coating | |
| HPMC (Methocel E5) | 1.440 |
| Polyethylene Glycol 6000 | 0.420 |
| Titanium dioxide | 0.600 |
| Talc | 0.514 |
| Iron oxide red | 0.026 |
| Total Film coated tablet | 133.000 |

K) Film coated tablet

| Constituents | mg/tablet |
|---|---|
| Core | |
| Flibanserin | 100.000 |
| Dibasic Calciumphosphate, anhydrous | 69.750 |
| Microcrystalline cellulose | 69.750 |
| HPMC (e.g. Methocel E5) | 2.750 |
| Carboxymethylcellulose sodium | 5.000 |
| Colloidal silicon dioxide | 1.250 |
| Magnesium stearate | 1.500 |
| Coating | |
| HPMC (e.g. Methocel E5) | 2.400 |
| Polyethylene Glycol 6000 | 0.700 |
| Titanium dioxide | 1.043 |
| Talc | 0.857 |
| Total Film coated tablet | 255.000 |

L) Film coated tablet

| Constituents | mg/tablet |
|---|---|
| Core | |
| Flibanserin | 20.000 |
| Lactose monohydrate | 130.000 |
| Microcrystalline cellulose | 43.100 |
| Hydroxypropyl Cellulose (e.g. Klucel LF) | 1.900 |
| Sodium Starch Glycolate | 4.000 |
| Magnesium stearate | 1.000 |
| Coating | |
| HPMC (e.g. Methocel E5) | 2.400 |
| Polyethylene Glycol 6000 | 0.700 |
| Titanium dioxide | 1.043 |
| Talc | 0.857 |
| Total Film coated tablet | 205.000 |

| M) | |
|---|---|
| Constituents | mg/tablet |
| Core | |
| Flibanserin (free base) | 50.000 |
| Orlistat | 120.000 |
| Anhydrous dibasic calcium phosphate | 100.000 |
| Microcrystalline cellulose | 203.090 |
| HPMC (Methocel E5) | 6.615 |
| Croscarmellose sodium | 8.820 |
| Magnesium stearate | 2.250 |
| Coating | |
| HPMC (Methocel E5) | 4.320 |
| Polyethylene Glycol 6000 | 1.260 |
| Titanium dioxide | 1.800 |
| Talc | 1.542 |
| Iron oxide red | 0.078 |
| Total Film coated tablet | 499.775 |

| Constituents | mg/tablet |
|---|---|
| N) Core: | |
| Flibanserin (free base) | 50.000 |
| Sibutramine | 10.000 |
| Lactose monohydrate | 133.750 |
| Microcrystalline cellulose | 40.000 |
| Hydroxypropylcellulose | 2.500 |
| Corn starch | 12.500 |
| Magnesium stearate | 1.250 |
| Coating | |
| HPMC (e.g. Pharmacoat 606) | 2.400 |
| Polyethylene Glycol 6000 | 0.700 |
| Titanium dioxide | 1.000 |
| Talc | 0.857 |
| Iron oxide yellow | 0.043 |
| Total Film coated tablet | 255.000 |

| O) | |
|---|---|
| Constituents | mg/tablet |
| Core | |
| Flibanserin (free base) | 50.000 |
| Phenetermine | 30.000 |
| Lactose monohydrate | 143.490 |
| Microcrystalline cellulose | 47.810 |
| HPMC (e.g. Pharmacoat 606) | 2.500 |
| Carboxymethylcellulose sodium | 5.000 |
| Mannitol | 60.000 |
| Corn starch | 36.500 |
| Povidone | 1.000 |
| Colloidal silicon dioxide | 1.000 |
| Magnesium stearate | 1.700 |
| Coating | |
| HPMC (e.g. Methocel E5) | 3.360 |
| Polyethylene Glycol 6000 | 0.980 |
| Titanium dioxide | 1.400 |
| Talc | 1.200 |
| Iron oxide red | 0.060 |
| Total Film coated bilayer tablet | 386.000 |

Pharmacological Experiments:

To test the efficacy of Flibanserin in the treatment of obesity groups of the rats per sex per group (gang-housed) received Flibanserin at dosages of 0 (control), 100, 200, and 600 mg/kg/day via dietary admixture. The test compound was mixed with the food to obtain a 3% premix. This premix was prepared in week −1 and drug week 7 and was used to prepare the substance/food mixtures for all individual groups. The substance/food concentration was calculated using the mean daily food intake from the study week before. The substance/food mixture was made weekly for every dose group and stored under darkness in the animal room. The concentration, homogeneity and stability of the test substance in the food was checked during study week 2 with reanalysis one and four weeks later. One further check of concentration and homogeneity was performed in week 13. The body weight of each animal was determined and recorded once a week including the pretest acclimation period, in the morning on the same day of the week.

The following tables presents the results of the above described experiments as absolute body weights at start of treatment (week −1) as well as in drug week 6 and 13, including percentage change compared to controls. (in parentheses).

TABLE 1

Table. Mean absolute body weights of males[#] in grams and percent change to controls

| Drug week | Dosage BIMT 17 BS (mg/kg/day) | | | |
|---|---|---|---|---|
| | 0 (Controls) | 100 | 200 | 600 |
| −1 | 191.3 | 188.1 (−1.7) | 189.3 (−1.0) | 186.8 (−2.4) |
| 6 | 368.2 | 340.9 (−7.4)↓ | 340.4 (−7.5)↓ | 284.8 (−22.7)↓ |
| 13 | 440.4 | 397.4 (−9.8)↓ | 400.9 (−9.0)↓ | 333.2 (−24.3)↓ |

↓significantly decreased compared to controls ($p < 0.05$; t-test, pooled variance)
[#]n = 10/group

TABLE 2

Table. Mean absolute body weights of females[#] in grams and percent change to controls

| Drug week | Dosage BIMT 17 BS (mg/kg/day) | | | |
|---|---|---|---|---|
| | 0 (Controls) | 100 | 200 | 600 |
| −1 | 141.2 | 141.3 (+0.1) | 142.2 (+0.7) | 140.7 (−0.4) |
| 6 | 229.1 | 213.6 (−6.8)↓ | 209.7 (−8.5)↓ | 196.0 (−14.4)↓ |
| 13 | 261.5 | 234.5 (−10.3)↓ | 234.9 (−10.2)↓ | 225.8 (−13.7)↓ |

↓significantly decreased compared to controls ($p < 0.05$; t-test, pooled variance)
[#]n = 10/group From Tables 1 and 2 it can be taken that the body weight gain of males and females were significantly decreased in almost all drug weeks. At study end the difference compared to controls was 10%, 9% and 24% in males and 10%, 10% and 14% in females at 100, 200 and 600 mg/kg/day, respectively.

This pharmacological data provide evidence for the efficacy of Flibanserin in the treatment of obesity and can be used for the preparation of a medicament for promoting, increasing or facilitating weight loss and for inhibiting or prevention of body weight gain.

The invention claimed is:

1. A method of treating obesity comprising administering to an individual in need thereof a therapeutically effective amount of flibanserin, or a pharmacologically acceptable acid addition salt thereof.

2. The method according to claim 1, wherein obesity comprises exogenic obesity, hyperinsulinaemic obesity, hyperplasmic obesity, hyperphyseal adiposity, hypoplasmic obesity, hypothyroid obesity, hypothalamic obesity, symptomatic obesity, infantile obesity, upper body obesity, alimentary obesity, hypogonadal obesity, or central obesity.

3. The method of claim 1, further comprising administering a second active ingredient comprising orlistat, phenetermine, sibutramine, or topiramate, or a pharmaceutical acceptable salt thereof.

4. The method of claim 1, further comprising administering a second active ingredient comprising ergoset, pramlintinide, leptin, BAY-27-9955, glipazide, glyburide, alprostadil, thipride hydrochloride, cilostazol, mexiletine hydrochloride, ethyl eicosapentate, memantine, or pimagedine, or a pharmaceutical acceptable salt thereof.

5. The method of claim 1, further comprising administering a second active ingredient comprising pioglitazone or a pharmaceutical acceptable salt thereof, troglitazone, rosiglitazone or a pharmaceutical acceptable salt thereof, JTT-501, GI-262570, MCC-555, YM-440, DRF-2593, BM-13-1258, KRP-297, R-119702, GW-1929, tolbutamide, chloropropamide, tolazamide, acetohexamide, glyclopyramide, an ammonium salt of glyclopyramide, glibenclamide, gliclazide, glimepiride, repaglinide, nateglinide, mitiglinide, JTT-608, metformin, bovine insulin, porcine insulin, semi-synthetic human insulin, genetically-engineered human insulin, acarbose, voglibose, miglitol, emiglitate, AJ-9677, BMS-196085, SB-226552, AZ40140, tolrestat, epalrestat, imirestat, zenarestat, SNK-860, zopolrestat, ARI-50i, AS-3201, NGF, LY-333531, LAF237, MK431, 815541, 823093, 825964, liraglutide, exenatide, AVE-2268, T-1095, mazindol, baiamine, NGD-95-1, lipstatin, rimonabant, phenylpropanolamine, ephedrine, pseudroephedrine, dexfenfluramine, fenfluramine, BVT.933, APD356, bromocriptine, pramipexol, dehydroepiandrosterone, exendin, AC 2993, CJC-1131, ZP10, GRT0203Y, captopril, enalapril, alacepril, delapril, lisinopril, imidapril, benazepril, cilazapril, temocapril, trandolapril, manidipine, nifedipine, amlodipine, efonidipine, nicardipine, levcromakalim, L-27152, AL0671, NIP-121, telmisartan, losartan, candesartan cilexetil, valsartan, irbesartan, CS-866, E4177, pravastatin or a pharmaceutical acceptable salt thereof, simvastatin or a pharmaceutical acceptable salt thereof, lovastatin or a pharmaceutical acceptable salt thereof, atorvastatin or a pharmaceutical acceptable salt thereof, fluvastatin or a pharmaceutical acceptable salt thereof, lipantil or a pharmaceutical acceptable salt thereof, cerivastatin or a pharmaceutical acceptable salt thereof, itavastatin or a pharmaceutical acceptable salt thereof, ZD-4522 or a pharmaceutical acceptable salt thereof, bezafibrate, clinofibrate, clofibrate, simfibrate, meloxicam, ibuprofen, or mixtures thereof.

* * * * *